United States Patent [19]

Miller et al.

[11] Patent Number: 4,671,290
[45] Date of Patent: Jun. 9, 1987

[54] AUTOMATIC TOURNIQUET

[75] Inventors: Scott Miller, Boulder, Colo.; Vann Frazier, Lauderdale Lakes, Fla.

[73] Assignee: Richards Medical Company, Memphis, Tenn.

[21] Appl. No.: 691,759

[22] Filed: Jan. 15, 1985

[51] Int. Cl.$^4$ .................. A61B 5/02; A61B 17/12
[52] U.S. Cl. ............................. 128/681; 128/327
[58] Field of Search .................. 128/327, 680–683

[56] References Cited

U.S. PATENT DOCUMENTS

| | | |
|---|---|---|
| 3,227,155 | 1/1966 | Erickson et al. |
| 3,552,383 | 1/1971 | Krueger et al. |
| 3,893,452 | 7/1975 | Birnbaum |
| 3,903,872 | 9/1975 | Link |
| 3,996,928 | 12/1976 | Marx |
| 4,009,709 | 3/1977 | Link et al. |
| 4,074,711 | 2/1978 | Link et al. |
| 4,105,021 | 8/1978 | Williams et al. |
| 4,137,907 | 2/1979 | Jansen et al. |
| 4,140,110 | 2/1979 | Jansen et al. |
| 4,154,238 | 5/1979 | Link |
| 4,169,463 | 10/1979 | Piquard ........................ 128/693 |
| 4,174,707 | 11/1979 | Link et al. |
| 4,190,886 | 2/1980 | Sherman |
| 4,263,918 | 4/1981 | Swearingen et al. |
| 4,271,843 | 6/1981 | Flynn ............................ 128/681 |
| 4,273,136 | 6/1981 | Kubo et al. |
| 4,321,929 | 3/1982 | Lemelson |
| 4,360,029 | 11/1982 | Ramsey, III .................. 128/681 |
| 4,367,751 | 1/1983 | Link et al. |
| 4,407,297 | 10/1983 | Croslin |
| 4,427,013 | 1/1984 | Nunn et al. .................... 128/681 |
| 4,461,266 | 7/1984 | Hood, Jr. et al. |
| 4,469,099 | 9/1984 | McEwen |
| 4,479,494 | 10/1984 | McEwen ........................ 128/327 |
| 4,517,986 | 5/1985 | Bilgutay |
| 4,548,198 | 10/1985 | Manes ............................ 128/327 |

OTHER PUBLICATIONS

Clark, N. G. "Pressure-Responsive Tourniquet", Published International Patent Application No. (PCT) WO 83/00995.
Dinamap Model 845 Operation Manual, Critikon, Inc., 1980, pp. 8–10.
McEwen & McGraw, An Adaptive Tourniquet for Improved Safety in Surgery, IEEE Transactions on Biomedical Eng., Feb. 1982, pp. 122–128.
McEwen, Complications of and Improvements in Pneumatic Tourniquets Used in Surgery, The Surgical Technologist, Jan. 1982, pp. 23–28.
McEwen & McGraw, An Automatic Tourniquet for Surgical Applications, 32nd Annual Conference on Engineering in Medicine and Biology, Oct. 6, 1979, p. 243.
McEwen, Wachsmuth, Fong & McGraw, Performance of a Microprocessor-Based Tourniquet in Surgery, Digest of 8th Canadian Medical and Biological Eng. Conf., Aug. 1980.
Sanders, The Tourniquet, Instrument or Weapon?, The Hand, vol. 5, No. 2, 1973, pp. 119–123.
Assoc. for the Advancement of Medical Instrumentation, Standard for Electronic or Automated Sphygmomanometers (Proposed), Aug. 1980.

Primary Examiner—Henry J. Recla
Assistant Examiner—Francis J. Jaworski
Attorney, Agent, or Firm—Pravel, Gambrell, Hewitt & Kimball

[57] ABSTRACT

A method and apparatus for measuring blood pressure and controlling the pressure of a pneumatic tourniquet at a desired level, either above the systolic blood pressure or at an absolute level.

12 Claims, 37 Drawing Figures

AUTOMATIC TOURNIQUET

BACKGROUND OF THE INVENTION

1. Field of the Invention:

The present invention relates to tourniquets, especially to tourniquets used to provide a bloodless field in surgery.

2. Description of the Prior Art:

Tourniquets have been used when performing surgery on the arms and legs to provide a bloodless field in the area of the operation and therefore greatly simplify the procedure. In the past, the use of excessive pressure to close off the blood vessels created a condition where injuries of several types, including limb paralysis and nerve damage, occurred. To avoid the deleterious effects of using a tourniquet, it was therefore desirable to use as low a tourniquet pressure as possible to stop blood flow to the limb. It was not practical or effective to use medically trained personnel to constantly monitor and adjust tourniquet pressure to maintain the bloodless field yet avoid tissue or nerve damage. To simplify the operation and reduce costs of the operation a system as automatic and error free as possible was needed so that personnel need not be assigned to monitor the tourniquet. The prior art moved in that direction but did resolve all the problems.

One prior vital signs monitor used a variation of the oscillometric method to measure blood pressure and heart rate. An inflatable blood pressure cuff was placed on the test subject and the cuff was inflated to a preset pressure. The monitor then used the incremental deflation technique to determine systolic, diastolic and mean arterial blood pressure. This device sought two equal value pressure pulses at each given cuff pressure, then deflated the cuff by one pressure increment. It then looked again for two equal value pressure pulses. If the pulses at the first several cuff pressures were not of near equal value, the device increased the pressure in the cuff and performed this check again. When it found several successive cuff pressures that showed equal value blood pressure pulses, it would begin its measuring sequence. It would deflate the cuff by the predetermined pressure increment and measure the value of the blood pressure pulses. When the blood pressure pulses started increasing in value, the device determined that this was the systolic blood pressure. When the pressure pulse value had been increasing and began decreasing, it determined that this was the mean arterial pressure. When the pulses stopped decreasing in value and leveled off, this was determined to be the diastolic blood pressure. This is the oscillometric technique coupled with incremental deflation to determine blood pressure. This device then displayed the determined blood pressures and heart rate.

While this variation of the oscillometric method did provide one method of determining blood pressure parameters, it was not reliable or accurate. These matters were, of course, significant since the patient's well being was being concerned. The prior art oscillometric method had a tendency to produce erroneous blood pressure readings. The blood pressure pulses were sufficiently variable, and the sampling and error checking limited enough, so that aberrant blood pressure results occured and it was necessary to repeat the test.

U.S. Pat. No. 4,321,929 disclosed an automatic tourniquet. This device relied upon sensing Korotkoff sounds, i.e., characteristic sounds made by blood flowing under pressure from the heart, to determine blood pressure. An inflatable cuff was placed over the subject. The cuff was then inflated until blood flow ceased, and the cuff was then gradually bled down to atmospheric pressure. When Korotkoff sounds were detected above a certain preset level, the pressure in the cuff was deemed to correspond to the systolic pressure. When the device stopped sensing Korotkoff sounds, the cuff pressure was equated to the diastolic pressure. The device then adjusted tourniquet pressure according to some unspecified relationship with the determined blood pressure.

U.S. Pat. No. 3,552,383 and English Pat. No. 1,253,501 also showed a blood pressure monitor. This device also used an inflatable blood pressure cuff and detected Korotkoff sounds to determine blood pressure values. This device tested for Korotkoff sounds at two different thresholds. If the sounds went from below level one through a middle region and above level two, the pressure in the cuff was equated to the systolic region and the systolic pressure was correlated to the cuff pressure where the sounds commenced. If the sounds went from above the higher level two through a middle region to below the lower level one, the pressure in the cuff was equated to the diastolic region and the diastolic pressure was determined to be the cuff pressure when the sounds stopped or went below the lower level. The device could increment or decrement the pressure in the cuff and did not rely on deflation-only operation. Even though this device sampled many heart beats at a given cuff pressure and required the Korotkoff sounds to be within a certain time after an EKG pulse corresponding to a heart beat its reliability and accuracy were insufficient to satisfy modern surgical needs.

Both this device and the previous device relied on sensing Korotkoff sounds. There were inherent problems with this approach. Korotkoff sounds were highly variable. They varied on a given person under different conditions and varied dramatically between individuals. This made any automatic approach very difficult and prone to errors. Simple devices, like the two discussed, were prone to errors and variability.

U.S. Pat. No. 4,469,099 disclosed a pneumatic tourniquet that used a pressure transducer and microprocessor to accurately maintain the desired, preset tourniquet pressure. The inventor had described the device in *Complications of and Improvements in Pneumatic Tourniquets used in Surgery*, Medical Instrumentation, July 1981, at 352. In the article he suggested that it might be possible to include an automatic sphygomomanometer with the tourniquet. He followed up on his suggestion and was issued in U.S. Pat. No. 4,479,494. This patent disclosed the use of a blood pressure sensor in combination with a controllable tourniquet to produce an adaptive pneumatic tourniquet. The patent did not disclose any new technique for sensing the blood pressure, but merely suggested the use of commonly available blood pressure monitors, one of which has been previously discussed. In this regard, see also an article entitled *An Adaptive Tourniquet for Improved Safety in Surgery*, IEEE Transactions on Biomedical Engineering, Vol. BME-29 No. 2, Feb. 1982, at 122.

The major problem with the prior art was a tendency to produce aberrant blood pressure readings with some frequency. If these aberrant readings were then used as a basis for an automatic control device to control tourniquet pressure, without human monitoring and intervention, problems resulted because the tourniquet responded to erroneous signals and did not operate as needed. With systems of the prior art, resolution of this aberrant reading problem required more time than was available and made the devices highly unresponsive to the changing conditions of the patient in the operating environment.

SUMMARY OF THE INVENTION

The method and apparatus of the present invention use a novel teohnique to eliminate erroneous blood pressure readinqs and whioh is suffioiently reliable to permit fully automatio oontrol of the tourniquet pressure. In the automatic mode, the present invention automatically measures blood pressure and maintains the tourniquet pressure at a level which is a prescribed amount above the measured blood pressure. The system may also be placed in the manual mode to maintain the cuff pressure at a preset pressure relative to atmospheric pressure.

The blood pressure is measured using an inflatable cuff to surround the limb of the subject which is inflated to a given pressure. The method and apparatus of the present invention then uses a novel variation of the oscillometric method to measure the blood pressure. A pressure sensor measures the average pressure resulting from a number of blood pulses on the cuff. A mean value of these sampled pressure readings is determined. This mean value is used to determine the mean deviation of the samples. The resulting mean deviation value is multiplied by a prescribed factor to increase the accuracy obtainable in later stages and an average amplitude of the blood pressure pulses for this interval is thereby generated. This technique greatly reduces the variations possible due to an erroneous instantaneous reading. The blood pressure cuff pressure is then decreased and the mean deviation procedure is repeated.

The method and apparatus of the present invention utilizes this acquired data in a least squares fit method based on four cuff pressure points to determine several conditions. To first qualify as a proper sample, the sample must have an average blood pressure cuff pressure of less pressure than the previous sample. If the cuff pressure is not decreasing, then another sample at a lower cuff pressure is taken and the last three samples plus the new sample are used to perform the same check. When the the last four blood pressure cuff sample pressures have been determined to be decreasing, the slope of the line going through these four samples is calculated using the least squares method. The slope of the line defined by the four acceptable data points is then checked to see if it is within allowable limits. This check further limits the possibility of erroneous readings. Once the tourniquet control of the present invention determines that the measured data satisfies these conditions, the actual systolic blood pressure of the subject is calculated by dividing the constant of the equation by the slope and using the magnitude of the result as the systolic blood pressure. The required tourniquet pressure is then derived by adding a prescribed amount of pressure that the tourniquet is to be set above systolic pressure to the calculated systolic blood pressure. The tourniquet pressure is adjusted and maintained at this level using the pressure sensor to measure the tourniquet pressure. At regular periodic intervals or on command the entire blood pressure determination and tourniquet pressure control method is repeated to provide safe and fully automatic tourniquet control.

Alarms are provided to warn the operator when the tourniquet is not operating properly and could cause an injury. If the tourniquet controller cannot obtain a blood pressure in three tries or if the obtained systolic blood pressure is less than 70 mmHg, an alarm sounds and the tourniquet pressure is maintained at 180 mmHg. If there is a kink in any of the hoses to the pressure cuff or tourniquet an alarm sounds and the current pressure is maintained. If the tourniquet controller cannot maintain the desired pressure within certain limits above or below the desired pressure an alarm sounds and the device keeps operating. An alarm sounds every fifteen minutes of operation to alert the operator to the total elapsed time.

DESCRIPTION OF THE PREFERRED EMBODIMENT

Table of Contents

I. Overview of Operation and Apparatus
II. Apparatus
III. Operation of the Apparatus
  A. Introduction
  B. Initialization
  C. Main Sequence
  D Timer Interrupt Sequence
  E. Monitoring and Controlling the Tourniquet Pressure
    1. Manual Mode Operation Sequences
      a. MANMODE Sequence
      b. ADJUST Sequence
      c. PUMP Sequence
      d. VENT Sequence
      e. ADJEND Sequence
      f. DISPRES Sequence
      g RDPRESS Sequence
      h. KINK Sequence
    2. Automatic Mode
      a. PONAUTO Sequence
      b. Systolic Blood Pressure Calculation
        i. Theoretical Basis
        ii. RDLIMB Sequence
    3. Off Mode
      a. OFFMODE Sequence
      b. RCHKOFF Sequence
      c. TSTBP Sequence
    4. Release
  F. Alarms 1. ALARM Sequence
2. TPALRM and BPALRM Sequences
G. Calibration of Controller C IV. Conclusion

I.

Overview of Operation and Apparatus

Figure 1:
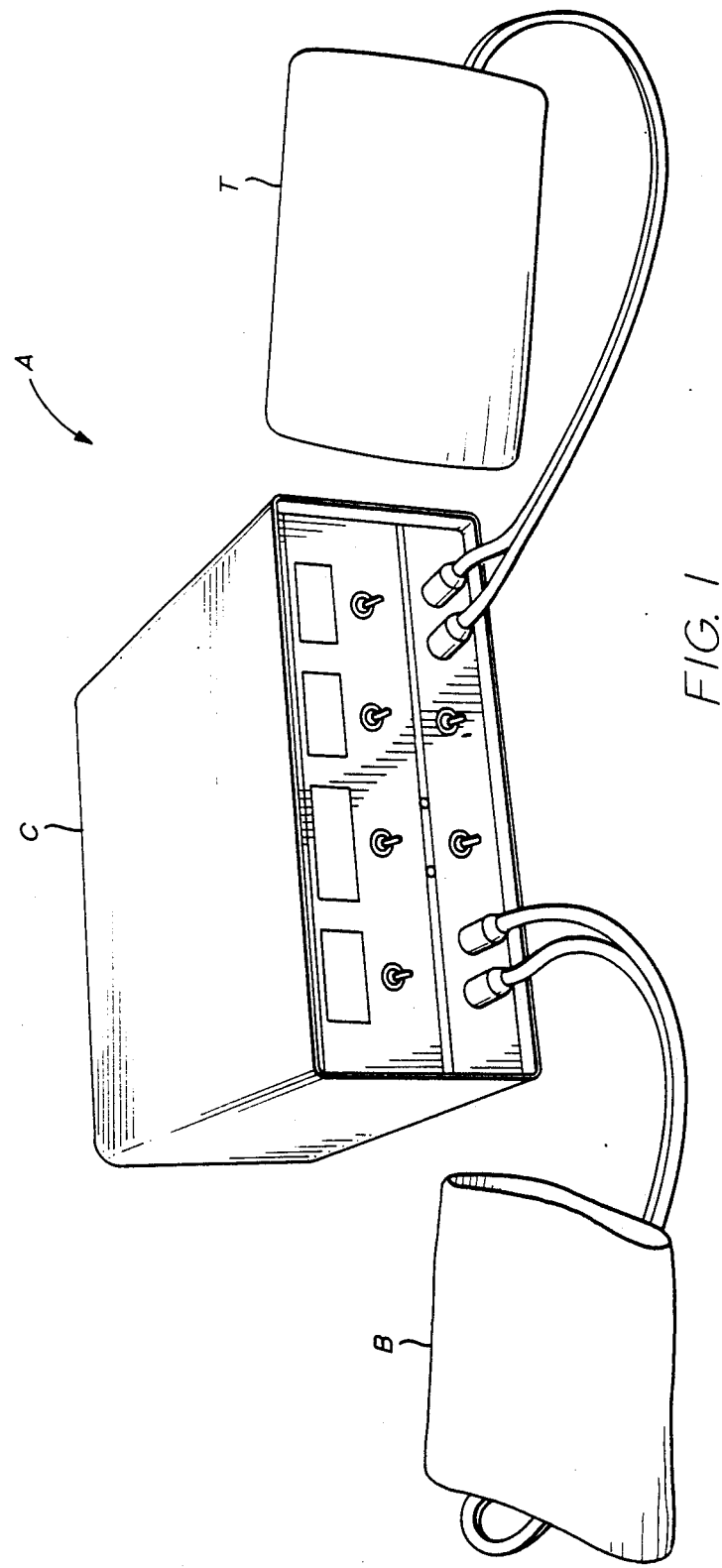
FIG. 1 is a perspective view of an apparatus according to the present invention.

Referring now to FIG. 1 the letter A represents generally the automatic tourniquet apparatus of the present invention. Blood pressure cuff B is placed on a limb, generally the arm, to be used for measuring blood pressure of the patient. Tourniquet T is placed around the limb which is the object of the surgical procedure. The controller C operates the blood pressure cuff B and the tourniquet T to provide safe and fully automatic control of tourniquet pressure.

There are three modes of operation of the automatic tourniquet A. The preferred mode is the fully automatic mode. In this mode the physician or operator prescribes the amount the tourniquet pressure is to exceed the actual systolic blood pressure of the patient by entering this value into the controller C. On command and at regular intervals the controller C inflates the blood pressure cuff B and determines the systolic blood pressure of the patient. After determining the systolic blood pressure of the patient the controller automatically sets the tourniquet pressure at the desired level above the patient's systolic blood pressure and maintains the tourniquet pressure at that level.

In the manual mode a desired tourniquet pressure is entered into the controller C, without reference to the patient's blood pressure. Controller C then maintains the tourniquet T pressure at the desired level.

In the off mode the controller checks the blood pressure on command and displays the tourniquet pressure but does not control the tourniquet pressure.

II.

Apparatus

Figure 2:
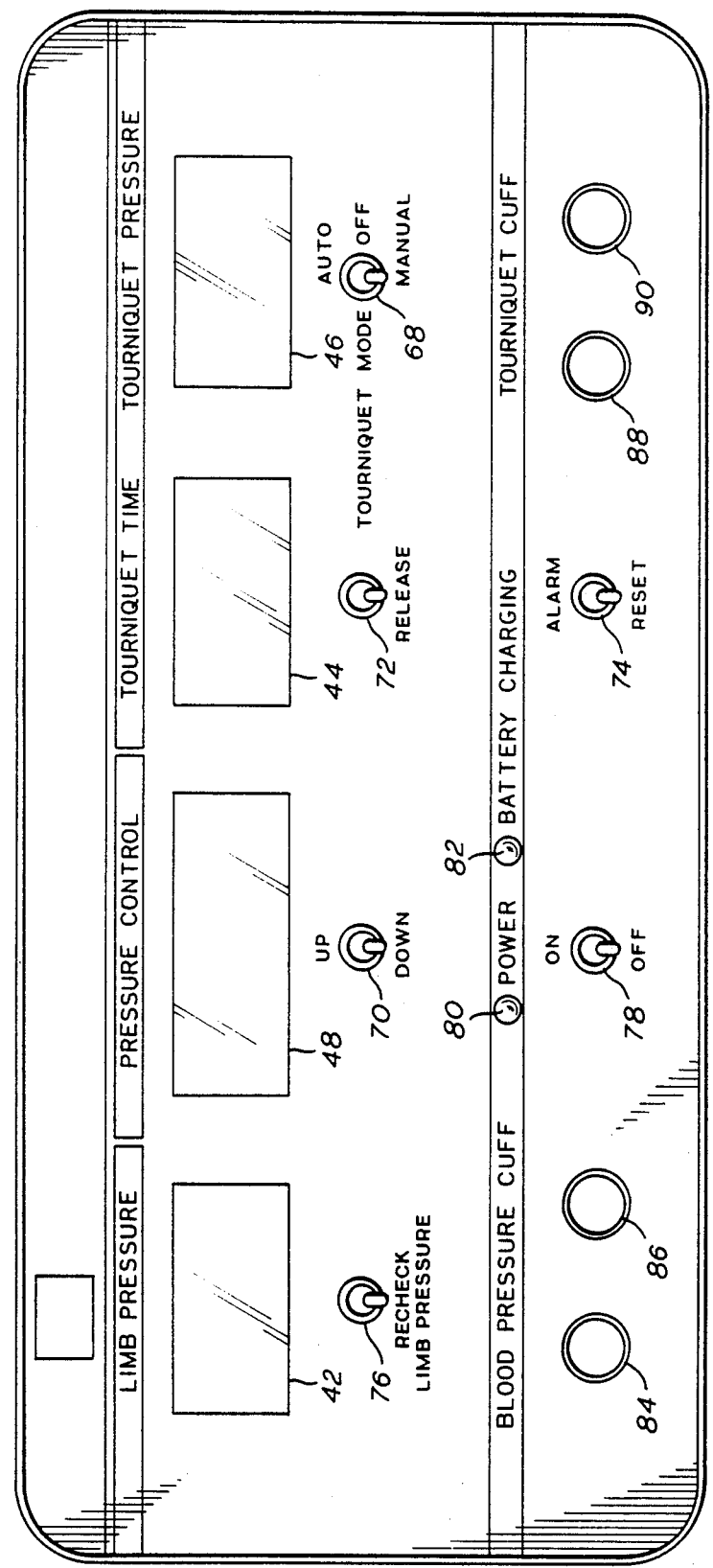
FIG. 2 is a front view of an apparatus according to the present invention.

The front panel of controller C is shown in FIG. 2. The systolic blood pressure of the patient is shown in the limb pressure display 42. Display 48 is the control display and has two purposes. Three digits display either the amount the tourniquet pressure is to be greater than the systolic limb pressure in the automatic mode or the desired tourniquet pressure in the manual mode. A plus sign in display 48 indicates operational status of the device. If the plus sign is displayed, the controller C is actively controlling and maintaining the tourniquet pressure at the desired level. If the plus sign is not displayed, the tourniquet T is either vented for release or has a fixed volume of air pressurizing it. The total amount of time the tourniquet has been inflated is shown in display 44. Display 46 is used to indicate the pressure in the tourniquet.

Switch 68 is used to control the mode of the apparatus as indicated in the overview. Switch 68 is a three-position switch that can be located in the automatic, manual or off modes depending upon the desired mode of operation. Switch 72 is the release switch, which is used to release the pressure from the tourniquet during off mode operation to allow blood to resume flowing in the limb. Switch 70 is a three-position switch used to set the pressure difference to be applied to the tourniquet. Holding switch 70 in the up position increases the pressure control value displayed in display 48, while holding switch 70 in the down position decreases the value. Recheck switch 76 is depressed to initiate a determination of the blood pressure of the patient in any mode. Power switch 78 controls the application of power to the control circuitry as will be explained later.

Light emitting diode (LED) 80 is illuminated whenever electrical power is provided to the control circuitry. Light emitting diode 82 indicates that the battery in the device, which is used to continue operation in case of a AC power failure, is being charged. Light emitting diode 82 also indicates a presence of AC power to the controller C. This will be seen more clearly in the description of the power supply. Alarm switch 74 is used to cancel an alarm that has been activated. When the operator uses switch 74, he is acknowledging the alarm.

Blood pressure cuff pump port 84 and blood pressure cuff sensor port 86 are used to attach the blood pressure cuff B to the controller C. Tourniquet cuff pump port 88 and tourniquet cuff sensor port 90 are pneumatic coupling ports which permit tourniquet T to be attached to controller C.

Figure 5:
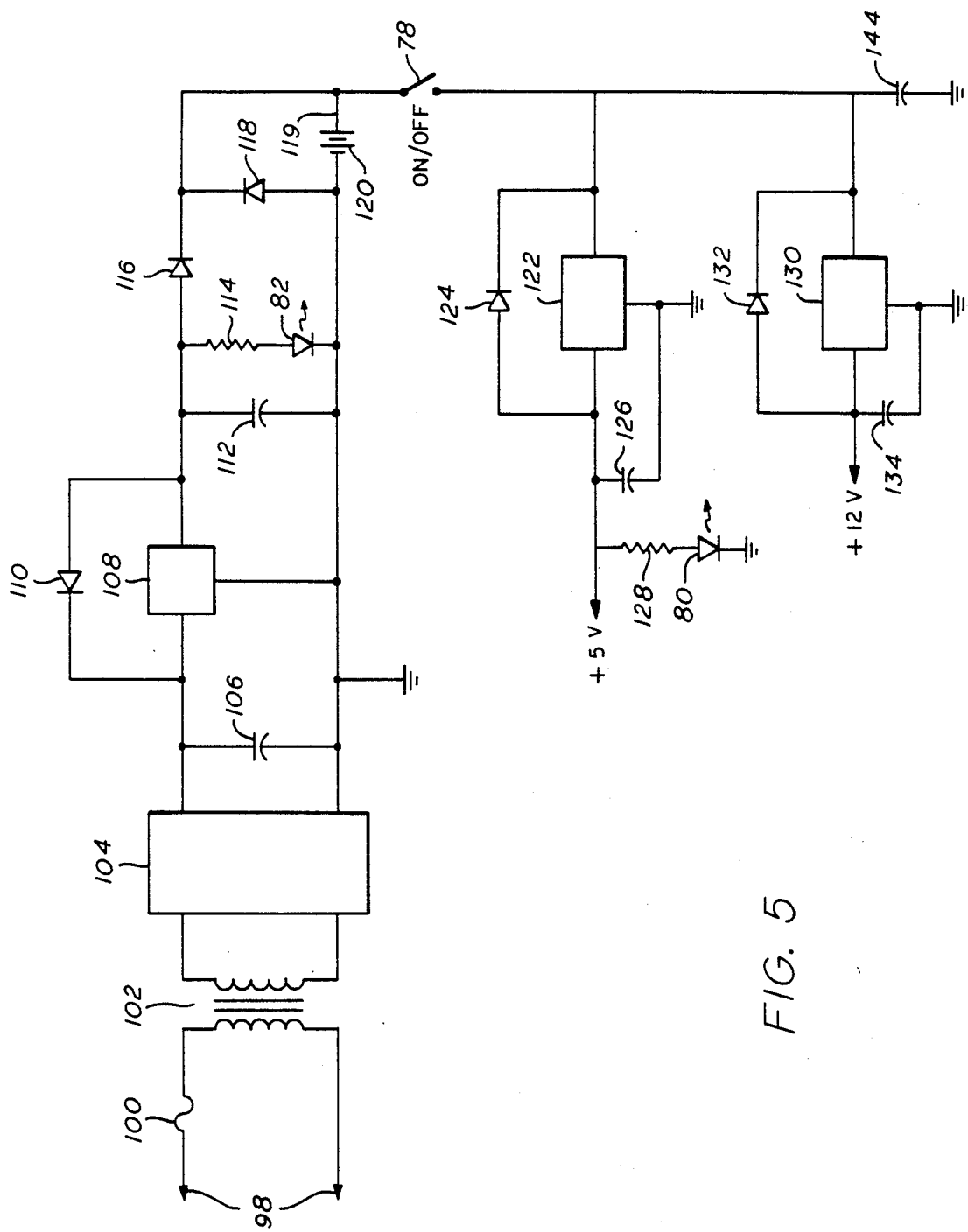
FIG. 5 is an electrical circuit schematic diagram of the power supply of an apparatus according to the present invention.

The power supply of the controller C is shown in FIG. 5. AC power plug 98 is connected to a standard source of 120 volt, 60 Hertz power. Fuse 100 is used to protect the AC power source and various internal components in the controller C from the presence of high current levels. Transformer 102 reduces the AC voltage applied to full-wave rectifier bridge 104. Capacitor 106 filters the output of rectifier bridge 104 for use with regulator 108. Regulator 108 has a nominal 15 volt output. Diode 110 provides input short circuit protection around regulator 108. Capacitor 112 is provided at the output of regulator 108 to ground to prevent oscillation of regulator 108. Resistor 114 and light emitting diode 82 connected from the output of regulator 108 to ground form a system condition circuit which provides a indication of whether battery 120 is being charged. When LED 82 is not illuminated there has been a failure in regulator 108 or a loss of supply voltage from plug 98.

Diode 116 is connected from the 15 volt supply line which is the output of regulator 108 to 12 volt battery 120, and provides battery 120 with a 14.3 charging voltage. Diode 116 also isolates the previously described power supply circuitry from the following power supply circuitry in case of an AC power failure. Battery 120 is connected between 14.3 volt line 119 and ground to provide a backup situation in case of AC power failure. Diode 118 is placed from 14.3 volt line 119 to ground to prevent damage to the circuitry in case of an accidental reverse connection of battery 120.

Power switch 78 is connected to 14.3 volt line 119. In the off position the power supply circuitry only charges battery 120. In the on position power is supplied from 14.3 volt line 119 to regulators 122 and 130 which provide regulated five and twelve volt supply voltage outputs respectively for use with various portions of the controller circuitry. Capacitor 144 is connected between the power switch 78 and ground to provide additional power supply filtering. Diodes 124 and 132 are connected from the outputs to the inputs of their respective regulators 122, 130 to protect against input short circuiting. Capacitor 126, 134 are provided at the output of regulator 122, 130 respectively to prevent oscillation.

Resistor 128 and light emitting diode 80 connected from the output of regulator 122 to ground form a power supply indicator circuit. Under normal operating conditions light emitting diodes 80 and 82 are both illuminated to indicate that the power supply and control circuitry are energized. Light emitting diode 80 will be off and light emitting diode 82 will be on when the battery charging circuit is energized but the remainder of the unit is inoperable. Light emitting diode 82 will be off and light emitting diode 80 on, when controller C is operating from the battery 120 and there has been a failure in the AC power supply line or the battery charging circuitry.

Figure 3:
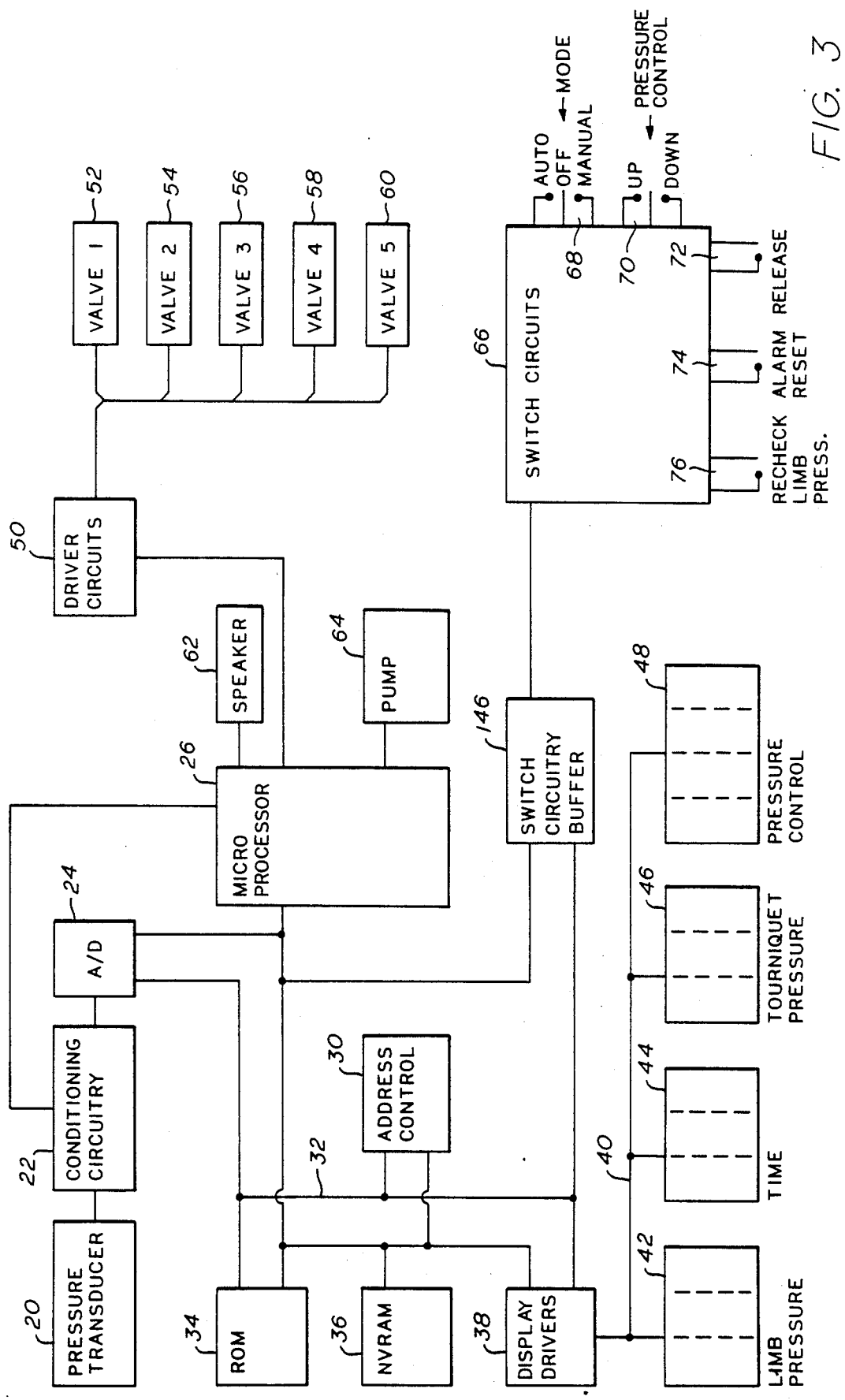
FIG. 3 is an electrical circuit block diagram of the control circuitry of an apparatus according to the present invention.

A block diagram of the control circuitry is shown in FIG. 3. A pressure transducer 20 provides an analog voltage output signal indicative of the pressure of the connected pneumatic source above ambient pressure. The output signal from transducer 20 is provided to analog conditioning circuit 22 for filtering and level shifting to obtain a signal that is essentially noise free and of the correct voltage level for interpretation by the analog to digital converter 24. Analog to digital converter 24 converts the conditioned pressure signal to a form suitable for interpretation by microprocessor 26.

Microprocessor 26 provides the data analysis and control functions for the controller C. Microprocessor 26 communicates with various peripheral devices via address/data bus 28. Address control circuitry 30 monitors the address/data bus 28 to determine which of the peripheral devices the microprocessor 26 is requesting and provides enabling control signals to the requested peripheral to permit access by microprocessor 26 in the conventional manner. Address control circuity 30 communicates with the peripheral devices via address control bus 32.

The instructions for the microprocessor 26 are contained in read only memory (ROM) 34. ROM 34 communicates with the microprocessor 26 via address/data bus 28 when the address control circuitry 30 determines that an access to the ROM 34 has been requested.

Also connected to the address/data bus 28 and controllable by the address control circuitry 30 is nonvolatile random access memory (NVRAM) 36. NVRAM 36 is used to contain preset characteristics and calibration constants required by the microprocessor 26 for correct operation. NVRAM 36 retains the data stored when power is removed.

Display drivers 38 are also connected to address/data bus 28 and enables microprocessor 26 to provide controlling operating data and status information to the operator via digital display elements 42–48. Display drivers 38 communicate with the displays 42–48 via display drive bus 40. By appropriately addressing the display drivers 38, microprocessor 26 can change any single digit in any of the four displays.

Switch circuitry 66 provides an interface between operator input switches 68–76 (FIG. 3) and microprocessor 26. Switch circuit 66 conditions the inputs received from switches 68–76 so as to be suitable for reading by microprocessor 26 via address/data bus 28 and switch circuitry buffer 146.

Microprocessor 26 issues control commands via a number of single bit output lines. One of these bits is used to control certain aspects of the conditioning circuity 22 to facilitate analog to digital conversion by converter 24 by triggering any amplification or change in the conditioning circuitry 22 to increase the apparent resolution of convertor 24 as may be necessary for proper operation of controller C. Another of these bits controls speaker 62 to provide audible operator signals as required by controller C. One of these bits is used to control pump 64 to supply air pressure to the tourniquet T and blood pressure cuff B. Five of the bit output lines are used to control pneumatic valve driver circuits 50 which drive the pneumatic valves 52–60 to control pressure in tourniquet T and cuff B upon command from microprocessor 26.

Microprocessor 26 also includes an internal timer which is set to issue an interrupt to the microprocessor 26 at prescribes intervals to cause microprocessor 26 to carry out specified control sequences at regular timed intervals.

Figure 4:
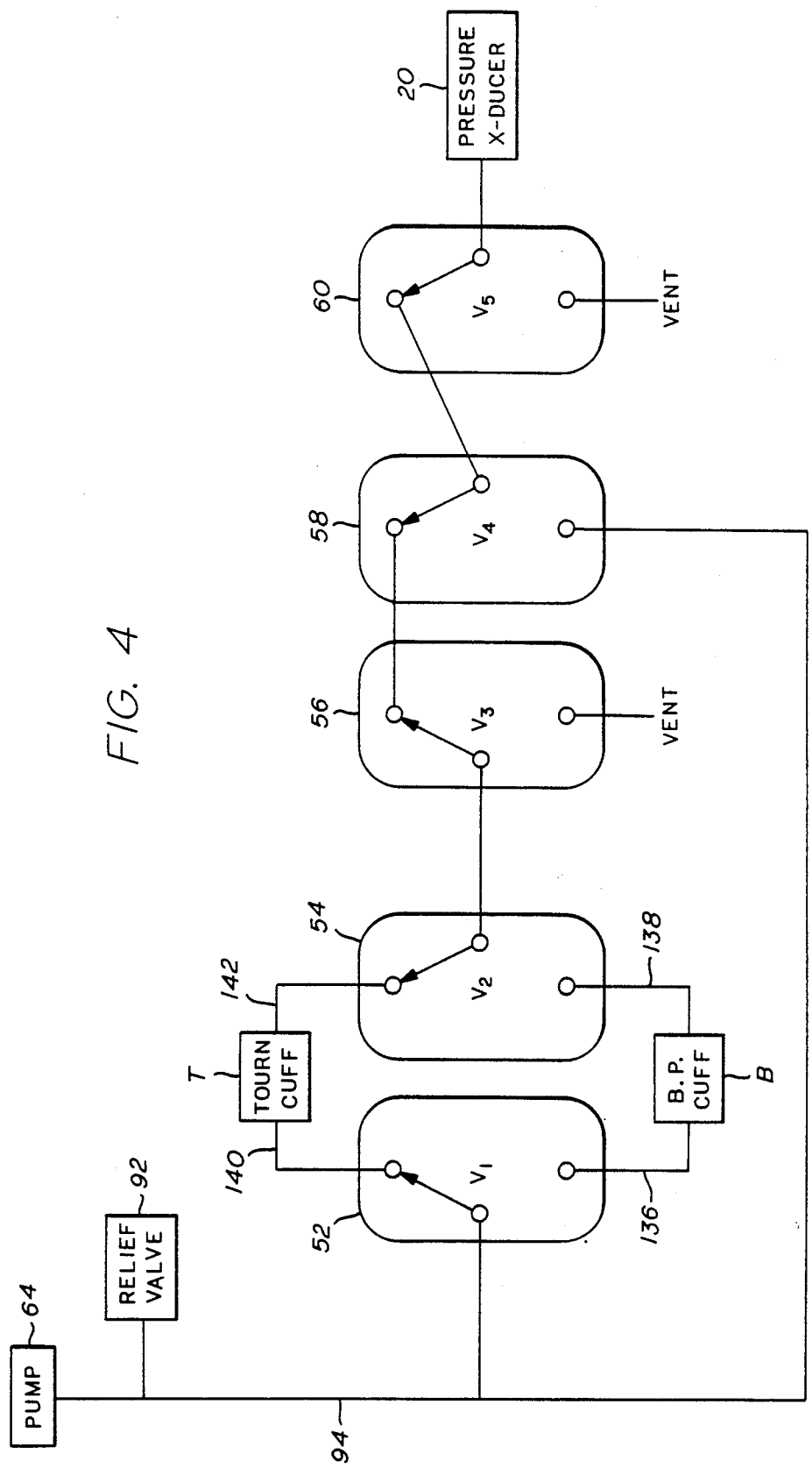
FIG. 4 is a pneumatic circuit schematic diagram of an apparatus according to the present invention.

Configuration of the pneumatic circuit which includes valves 52-50 is shown in FIG. 4. Pump 64 is connected to pump line 94. Also connected to pump line 94 is pressure relief valve 92. Pressure relief valve 92 is used as a fail-safe in case the pressure in line 94 exceeds the relief setting of relief valve 92. Pneumatic valves 52–60 are solenoid operated, two position valves and are shown in the unenergized or normally off position. When pneumatic valves 52–60 are energized they use the alternate flow path shown. For example, when pneumatic valve 52 is in the nonenergized position pressure flows from pump line 94 through pneumatic valve 52 to tourniquet cuff pump line 140 to tourniquet T and returns in tourniquet cuff sensor line 142 through valves 54–60 to pressure transducer 20.

If pneumatic valve 52 were energized, pressure would flow from pump line 94 through pneumatic valve 52 to blood pressure cuff line 136 through blood pressure cuff B to blood pressure cuff sensor line 138 and stop at valve 54 because the port at valve 54 is closed because valve 54 is in the off condition. In this state the air pump would be pressurizing blood pressure cuff B and the pressure transducer 20 would be sensing the pressure of the air in tourniquet T. Therefore it can be seen that the state of pneumatic valve 52 determines whether blood pressure cuff B or tourniquet cuff T is being pressurized. A condition where all valves are off is the tourniquet pressurize and sense condition. When valves 52 and 54 are energized and the remaining valves are off the blood pressure cuff pressure is being sensed.

Valve 56 is a vent valve. By energizing valve 56 the air in either the tourniquet T or blood pressure cuff B, depending upon the state of valve 54, is vented to the atmosphere.

Valve 58 is a kink valve. If there is a kink in one of the lines to tourniquet T or cuff B, the pressure in the two lines will be dissimilar. This is checked by reading the pressure in the appropriate cuff sense line with valve 58 in the off state. Energizing valve 58 allows the pressure transducer 20 to read the pressure in the pump line 94. If the difference is above a given margin, a kink exists and microprocessor 26 executes a prescribed control sequence to cause an alarm and set the tourniquet pressure at a safe level.

Valve 60 is a pressure transducer valve. When valve 60 is in the off state pressure transducer 20 is connected to valve 58. When valve 60 is in the on state pressure transducer 20 is connected to atmospheric pressure to provide the zero pressure readings necessary for calibration of the controller C.

III.

Operation of the Apparatus

A. Introduction

Microprocessor 26 monitors and controls the apparatus A by executing prescribed command sequences which form a control program for microprocessor 26.

The details of the control program are illustrated in flowchart form in FIGS. 7 to 27. During normal operation, microprocessor 26 is executing a loop of steps as determined by the selected mode of the device. Every 6.67 milliseconds the execution is interrupted and a timer interrupt sequence 420 is executed. Control will either be returned to the point in the appropriate loop where execution was interrupted or will enter the main sequence 288 to redetermine the correct sequence of operations for the revised mode of operation desired. Microprocessor 26 will then enter and continue the appropriate loop except when regularly interrupted by the timer.

For purposes of this description the operation of the sequences will be described in sequential order, as the steps naturally follow one another, unless a branch in the logic flow is indicated.

B. Initialization

Figure 7A:
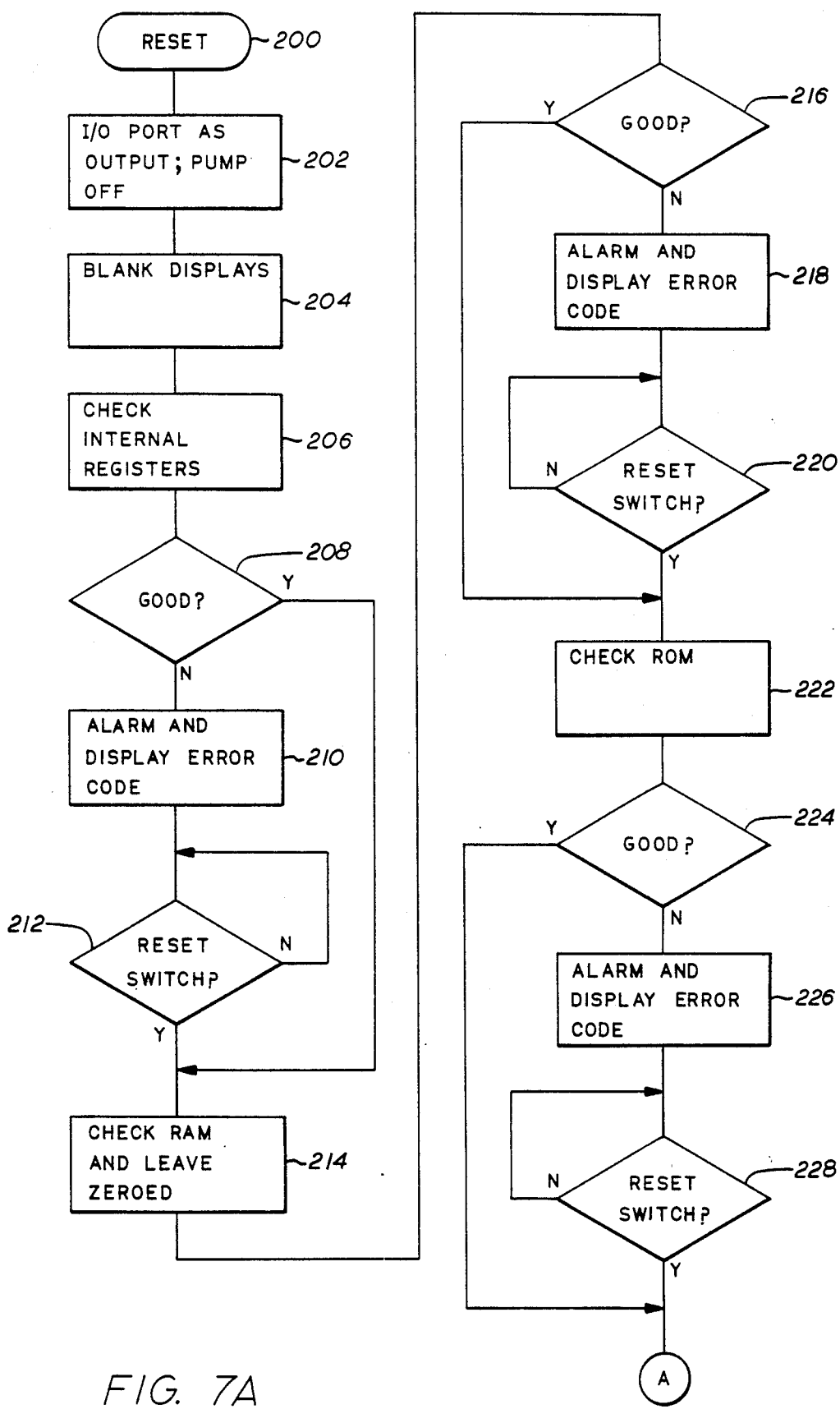
FIGS. 7–27 are schematic flow chart illustrations of portions of the operating sequence of the method and apparatus according to the present invention.
Figure 7B:
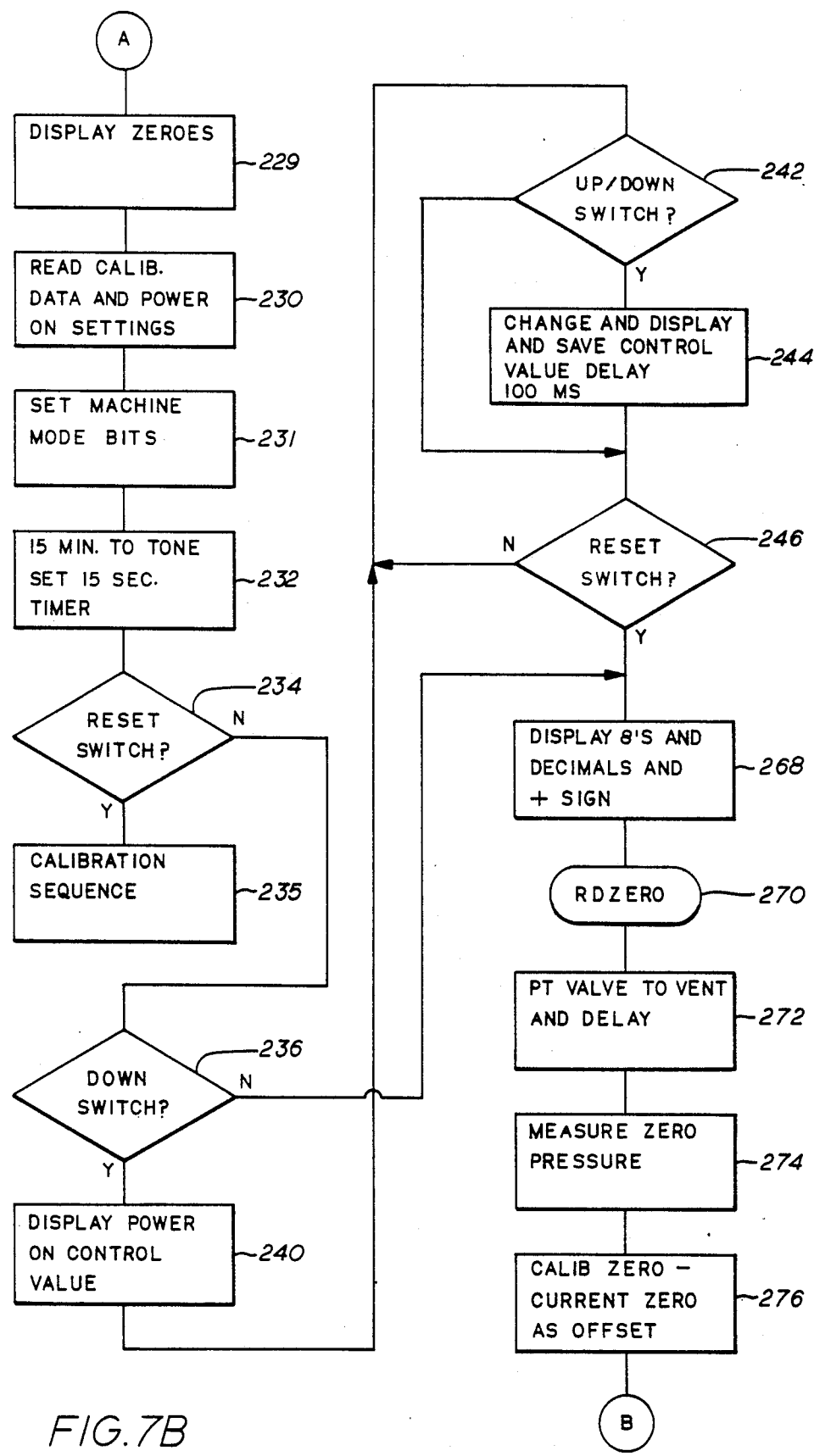
Figure 7C:
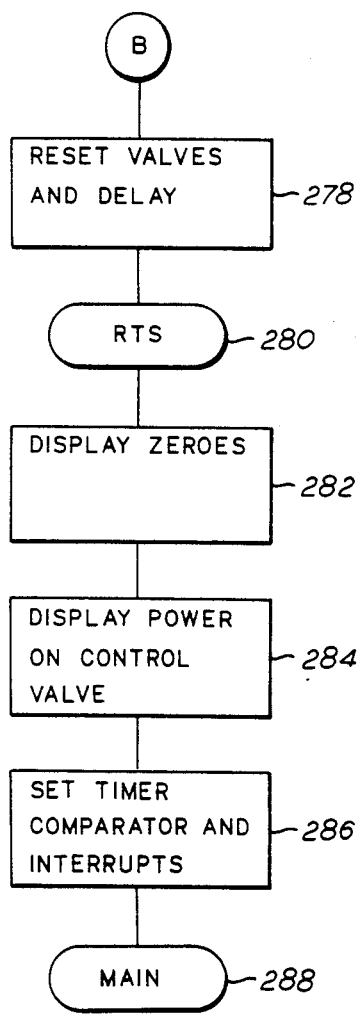

Referring now to FIGS. 7A, 7B, 7C, upon power up, microprocessor 26 fetches the reset vector and branches to the reset sequence 200. In step 202 microprocessor 26 configures its input/output port as an output port, pump 64 and speaker 62 are turned off and valves 54-58 are energized. Blanks are displayed on all displays in step 204.

The next series of steps is a check of the memory in the controller C. Step 206 checks the internal registers. If they are functional, step 208 transfers control to step 214. If the internal registers are not functional, step 208 transfers control to step 210 which sounds an alarm and displays the error code indicating internal register failure. The control sequence then loops at step 212 until the reset switch 74 has been actuated to acknowledge operator recognition of the malfunction. Control then proceeds to step 214 which is a check of all internal and external random access memory (RAM) which also clears the RAM to zeroes at the end of the step. If the RAM is satisfactory step 216 transfers control to step 222. If the RAM has tested nonfunctional, step 216 transfers control to step 218 which sounds an alarm and displays the RAM failure error code. The sequence loops at step 220 until the reset switch 74 is actuated by an operator to acknowledge the malfunction. Control then proceeds to step 222 where the system read only memory (ROM) is tested. If the ROM is satisfactory, control is passed via step 224 to step 229. Otherwise, step 226 sounds an alarm, displays the ROM malfunction error code and waits for the reset switch 74 in step 228.

Step 229 displays zeroes in all display locations. Step 230 reads the calibration data and power on settings from NVRAM 36. In step 231 the machine mode is tested and the appropriate bit is set to indicate the desired mode of operation to the main control sequence. Step 232 sets various other initialization parameters. The 15 minutes to tone timer is set and the 15 second timer is initialized. Step 234 tests the condition of reset switch 74. If reset switch 74 is enabled, control is passed to the calibrate sequence 300 in step 235. The calibrate sequence 300 will be described in detail later. If reset switch 74 is not set, control is transferred to step 236 from step 234. If switch 70 is not in the down position, step 236 transfers control to step 268. If switch 70 is down, control is passed to step 240 which displays the current power on control value in the control display. The power on control value is the value that is stored in NVRAM 36 and is the default value for the amount the tourniquet T will be pressurized greater than the patient's systolic blood pressure. If switch 70 is in an on position, step 242 transfers control to step 244 which increments or decrements the control value as desired, saves the new power on control value in the NVRAM 36, displays the new power on control value and produces a 100 millisecond delay to allow for user response. Control proceeds to step 246, which is where control passes if switch 70 is off in step 242. Step 246 then examines reset switch 74. If reset switch 74 is not on, control is passed to step 242 forming a loop. When reset switch 74 is on, step 246 transfers control to step 268.

Step 268 displays all segments and decimal points in the displays to indicate their functional status. Control is then passed to the RDZERO sequence 270. The first step in this sequence, step 272, sets the pressure transducer valve 60 to the vent position and waits for the valve to settle. In step 274 the zero or atmospheric pressure is tested. In step 276 this measured zero pressure is subtracted from the zero pressure value obtained from the calibration data previously recalled from the NVRAM 36 to determine the zero pressure offset value to be used during this operating interval. Valves 52-60 are reset to their standard off position and step 278 provides a delay to allow the valves to settle. Step 280 then returns control to the calling sequence which causes all zeroes to be displayed without any plus or minus sign or decimal points as an initialization read out for the operator. The power on control value is displayed in the control display 48 in step 284. Step 286 prepares the timer for operation. Control then passes to the main control sequence 288 to begin active tourinquet control.

To change the power on parameters for the control value the apparatus is energized with switch 70 in the down position. Switch 70 is then put in the appropriate position to increase or decrease the control value as desired. Actuation of reset switch 74 by the operator causes controller C to proceed with the initialization.

C. Main Sequence

The main sequence 288 (FIG. 8) performs the task of selecting the correct mode of operation and the correct control sequence for controller C. Main control sequence 288 is entered from either reset sequence 200 or timer sequence 420. Control is received from reset sequence 200 by direct flow while control is received from timer sequence 420 by means of an interrupt set by timer sequence 420 and activated upon the return from timer sequence 420 to the interrupted step.

Step 380 resets the interrupts, turns off the air pump 64 and speaker 62 and vents the blood pressure cuff B to the atmosphere.

Step 382 then determines which of the three modes of operation is desired by causing microprocessor 26 to read the position of the mode switch 68. If the manual mode is selected, control is passed to the manmode control sequence 384.

If the automatic mode of operation is desired, step 396 causes microprocessor 26 to determine if a recheck of the blood pressure has been requested by the operator. If recheck switch 76 is off, step 398 checks to see if the main sequence 288 has been entered on reset sequence 200 or the timer interrupt sequence 420. If main sequence 288 has been entered from reset sequence 200, control proceeds to PONAUTO sequence 400 which in turn passes control to AUTOMOD sequence 402. If main sequence 288 has been entered from timer interrupt sequence 420, control is passed to AUTOMOD sequence 402.

If recheck switch 76 is enabled, step 396 passes control to RCKAUTO sequence 404 which in turn passes control to AUTOMOD sequence 402.

If step 382 has determined that the desired mode is the off mode, control is passed to step 386 which interrogates the status of release switch 72. If release switch 72 is on, control is passed to RELEASE sequence 388. If release switch 72 is off, recheck switch 76 is then checked in step 390. If recheck switch 76 is on, RCHKOFF sequence 392 is performed followed by OFFMODE sequence 394. If recheck switch 76 is off, control proceeds directly to OFFMODE sequence 394.

The four sequences MANMODE 384, RELEASE 388, OFFMODE 394 and AUTOMOD 402 all form self contained loops. The only way to exit one of these loops is by changing a front panel switch which is polled by timer interrupt sequence 420.

D. Timer Interrupt Sequence

Microprocessor 26 contains a timer which is able to interrupt microprocessor 26 at given desired intervals. In this case the timer is conditioned to provide an interrupt every 6.67 milliseconds. As each interrupt is issued microprocessor control is transferred to timer interrupt sequence 420 (FIGS. 9A, 9B, 9C) which causes microcprocessor 26 to poll the operator interface switches and perform other regularly timed functions. The front panel switch positions are determined in step 422. Step 424 then causes microprocessor 26 to determine if any of the switches have changed positions. If the positions have changed, step 426 generates the interrupt that will cause the control flow to return to the main program sequence 288 upon return from the timer interrupt sequence 420. Control is not interrupted at this time because the interrupts are disabled while an interrupt sequence is executing.

Step 428 sets various flags in the apparatus to indicate the switch status to limit the processing required by main program sequence 288. Control then proceeds to step 430 which is also the step performed if the switch position has not changed. Step 430 clears the interrupt that has been issued by the timer thereby stopping any possible looping. Step 432 increments the first timer interrupt counter register which has been named TIMCNT. If the time count register does not equal 15, control flows to step 472, otherwise step 436 increments a second timer interrupt counter register, called TENTHS for tenths of a second. If the TENTHS register does not equal ten, step 438 transfers control to step 472.

If TENTHS register does equal ten, control is transferred to step 440 where the vent delay timer VENTDLY and the LPRES registers are decremented. The vent delay timer provides the operator with a two minute delay during which any regulation attempts are prevented if the tourniquet pressure is greater than 15 mmHg above the desired regulation point. This two minute delay amy be actuated by the operator, for example, to allow for transients induced in the tourniquet pressure due to moving the limb of the patient around as is often necessary. If this interval did not exist, the unit would attempt to compensate for the movement of the limb which might increase tourniquet pressure readings and therefore reduce the actual regulation point desired. LPRES is a 5-minute timer register used in automatic mode to reinitiate a blood pressure reading.

Control transfers from step 440 to step 442 which increments the DISPCNT, KINKFLG FIFTEEN and SECOND registers. DISPCNT is a two-second register used to compare current display values with desired display values to see if the displays need to be updated to desired values. KINKFLG is a 20-second register used to measure the delay required on a vent or pump cycle before a test is made to see if the lines are kinked. FIFTEEN is a register used in leak detection and is incremented once a second. SECOND is a register that is the seconds counter. If the FIFTEEN counter register equals 15, step 444 passes control to step 446 which clears the FIFTEEN register and the PASSCNT register. PASSCNT is a counter to indicate the number of times the pump is started within a given 15-second interval. If five pump cycles have started within the last 15 seconds, this is determined to be a leak condition and appropriate action is taken. If the FIFTEEN register is not equal to fifteen or following step 446, control is passed on step 447.

Step 447 tests to see if the elapsed time display 44 is disabled. If the elapsed time is disabled, the decimal point in the display 44 is shut off in step 448. If the elapsed time display 44 is enabled and it is an even second, step 450 sets a software flip flop to indicate that the decimal point should be turned on. If it is an odd second, the software flip flop is cleared by step 450 to indicate that the decimal point should be turned off. The decimal point in the timer display therefore flashes on and off at a two second interval. After the desired software flip flop state has been determined in step 450 or the decimal point display has been shut off in step 448, the elapsed time is displayed in step 4S2. If the value of the SECOND register is not 60 in step 454, control proceeds to step 472. If 60 seconds have elapsed, a check is made in step 456 to see if the elapsed timer is disabled. If the elapsed timer is disabled, control proceeds to step 472, otherwise the minute counter is incremented in step 458. If the minute counter has reached 240, step 460 sends control to step 462 which clears the minute counter. If the minute counter has been cleared or if the minute counter does not need clearing, control proceeds to step 464 which displays the elapsed time. The 15-minute timer, LTONE is decremented in step 466. This is a timer to indicate a beep every 15 minutes to warn the operator of the passage of this period of time and to notice the total elapsed time. Then step 468 checks to see if the LTONE register has been decremented to zero. If it has, step 470 creates the beep to indicate 15 minutes has elapsed and control proceeds to step 472. If the timer has not decremented to zero, control proceeds directly from step 468 to step 472.

Step 472 tests the status of the switch 70. If it is off, the flags PCONFLG and SPEED2 are cleared in step 474 and control proceeds to step 492. These two flags are used to indicate the increment rate of the value being affected by switch 70. Initially holding switch 70 in the up or down position causes the value to change at a relatively slow rate. After a change of ten counts as indicated by the interaction of PCONFLG and SPEED2 values, the rate at which the value changes is significantly increased, thereby reducing the time required to reach a desired value. The value displayed in the pressure control display 48 can be changed at any time by using the switch 70. This value is either the desired tourniquet pressure in manual mode or the incremental pressure above the systolic blood pressure in the automatic mode. The change in the value that occurs will be reflected and acted upon in the active mode sequence at the appropriate time.

If the switch 70 is active, step 476 checks to see if the SPEED2 flag is equal to 10. This flag value will equal ten when the value has been changed ten values and the high speed counting mode is active. If it is not, step 486 checks to see see if PCONFLG is equal to zero. PCONFLG will equal zero when it is time to adjust the value. If PCONFLG is equal to zero, control is passed to step 482. If PCONFLG is not equal to zero, step 488 checks to see if PCONFLG equals 30. If it is equal to 30, indicating that it is time to ad the value in the slow speed counting mode, step 490 clears PCONFLG and increments SPEED 2 and control is passed to step 482. If PCONFLAG does not equal 30 in step 488, control is passed to step 484.

If the SPEED2 flag in step 476 is tested and does equal 10 indicating that high speed operation is in effect, a check is made by step 478 to see if PCONFLG equals four. If PCONFLG does not equal four, transfer is passed to step 484. If it does equal four, step 480 clears PCONFLG. After clearing the PCONFLG, control is passed to step 482 which is used to adjust the control value using the PCONT2 sequence 342. After adjusting the pressure control value, step 484 is performed which increments PCONFLG and transfers control to step 492. Step 492 is a return from the timer interrupt sequence 420 to either the main program sequence 288 or the step at which the control sequence was interrupted by the timer interrupt.

E. Monitoring and Controlling the Tourniquet Pressure

1. Manual mode operation a. MANMODE sequence

The MANMODE sequence 384 is (FIG. 10) entered upon operator selection of manual mode and used to set the tourniquet pressure at a given desired pressure and to maintain the tourniquet pressure at that level irrespective of the patient's blood pressure. MANMODE sequence 384 begins by transferring control of microprocessor 26 to step 502 which blanks blood pressure display 42. Step 504 then tests to see if the power was just turned on. If the power was just turned on, step 506 creates a two-second delay. After the two-second delay control proceeds to step 508, which is also where control is passed if the power had been previously turned on. In step 508 the appropriate flag is set to turn on the elapsed timer to indicate the time tourniquet T has been inflated. In step 510 pneumatic valves 52–60 are set for the tourniquet position. Step 512 sets the variable CONTROL equal to the desired tourniquet pressure value and transfers control to step 514. Step 514 transfers control to be the ADJUST tourniquet subroutine 520. The ADJUST sequence 520 causes microprocessor 26 to adjust tourniquet T to the desired touriquet pressure value now equal to the variable CONTROL. Sequence 520 will be discussed in greater detail later. After tourniquet T has been adjusted to the correct pressure, step 516 transfers control to TSTBP subroutine 1070 which causes microprocessor 26 to determine whether there is a positive pressure in blood pressure cuff B and, if so, vent blood pressure cuff B. When control returns from TSTBP subroutine 1070, control is passed by step 518 to KINK subroutine 760 which causes microprocessor 26 to determine if one of the hoses to tourniquet T is blocked. After returning from this sequence, control is passed to step 512 to form a loop. The MANMODE sequence 384 stays in this four step loop until the mode switch 68 on the front panel has been changed.

b. ADJUST Sequence

ADJUST sequence 520 (FIG. 11) causes microprocessor 26 to adjust the pressure of tourniquet T or blood pressure cuff B to the desired value. Pneumatic valves 52–60 are set to effect the desired cuff before control is transferred to sequence 520. Sequence 520 begins by clearing a number of flags necessary for its operation in step 522, namely KINKFLG, ALRMCNT, DISPCNT, CONTFLG and PUMPFLG. In step 524 a test is performed to see if the desired tourniquet pressure value as indicated in CONTROL has changed. If it has changed, CONTFLG is set in step 526. After CONTFLG has been set or if the desired value has not changed, the current tourniquet pressure is read by the RDPRESS routine 730 in step 528. The RDPRESS sequence 730 will be explained in greater detail later.

Step 530 subtracts the desired tourniquet pressure value from the currently read pressure and checks to see if the resultant value is non-negative. If the resultant value is not non-negative, this means that the actual pressure may be less than the desired value and the machine sets the pump flag in step 532. Control proceeds to step 534 which subtracts the current pressure from the desired value and determines if this result is non-negative. If the result is not non-negative, this means that the current pressure is equal to the desired value and control proceeds to the ADJEND sequence 536. If the result is non-negative to either step 534 or step 530, control passes to step 538.

Step 538 checks to see if the result of the previous subtraction was zero. If the result was zero, control is passed to step 540 which clears VENTFLG to indicate that no venting is required. Control is then passed to sequence ADJEND 536. If the result of step 538 indicated that the subtraction result was not zero, step 542 subtracts five from the result of the previous subtraction. This five mmHg is the allowable plus or minus tolerance of the tourniquet pressure. If the result is negative or zero, this means that the tourniquet pressure is within allowable tolerances and control proceeds to step 540 and to ADJEND sequence 536.

If the current tourniquet pressure is more than 5 mmHg from the desired value as determined in step 542, control proceeds to step 544 which tests to see if PUMPFLG has been previously set. If PUMPFLG has been set, control is passed to PUMP sequence 540. If PUMPFLG has not been set, control proceeds to step 548 which tests to see if VENTFLG has been set. If VENTFLG has been set, control is passed to the VENT sequence 556. If VENTFLG has not been set, step 550 tests the CONTFLG to see if the desired value of the tourniquet pressure has been changed. If it has, control is passed to VENT sequence 556. If the desired pressure has not been changed, step 552 tests to see if the vent delay time as kept in VENTDLY is over. If the vent delay time is over, control is passed to the VENT sequence 556. If the vent time is not over, control is returned to the calling sequence in step 554.

c. PUMP Sequence

The PUMP sequence 546 (FIG. 12A, 12B) is used to actually control air pump 64 which pressurizes blood pressure cuff B or tourniquet T. The first action is to turn on air pump 64 in step 560. Next DISPRES sequence 700 is called in step 562 to display the tourniquet pressure in tourniquet pressure display 46. If the tourniquet pressure is less than 20 mmHg, control is transferred to step 566. Step 566 checks to see if 20 seconds has elapsed since the pump started pumping. If the 20 second period has not elapsed, control proceeds to step 588 which will be discussed in detail later. If 20 seconds has elapsed there is a major leak and control proceeds to step 568 which triggers the appropriate alarm using ALARM sequence 1170. Control then proceeds to step 570 which clears KINKFLG and transfers control to step 588.

If the pressure is greater than 20 mmHg in step 564, step 572 is performed which checks to see if DISPCNT is equal to one. If it is not equal to one, control passes to step 588. If it is equal to one, control passes to step 580 which subtracts the last pressure value stored in LSTPRES from the current pressure value to see if the pressure has changed. If the resulting value is positive, control is passed to step 588. If the resulting value from the subtraction is zero or negative, this indicates a possible kink condition and control is passed to step 582 which increments an alarm counter, ALRMCNT. Control passes to step 586 which checks to see if the alarm counter has reached 70. If it has not, control is passed to step 588. If the alarm counter does equal 70, control is passed to step 592. Step 592 is a call to the ALARM sequence 1170. After returning from the ALARM sequence 1170, control is passed to step 594 which clears ALRMCNT, DISPCNT, LASTPRES and LEAKFLG. Control is then passed to step 588.

Step 588 tests to see if the controller C is in the manual mode. If it is in the manual mode, control proceeds to step 596 which subtracts the desired pressure from the current value and proceeds to step 604. If the apparatus is not in the manual mode, control is passed to step 598 which tests the status of the value DISPFLG to see if the tourniquet pressure or the blood pressure cuff pressure is being controlled at that time. If it is the blood pressure, step 600 adds the last blood pressure reading and the desired incremental pressure to produce the desired control or tourniquet value. Control then proceeds to step 602. If the pressure being controlled is the tourniquet pressure, control proceeds directly from step 598 to step 602.

Step 602 subtracts the control or desired value from the current pressure reading and proceeds to step 604. If the result from the subtraction of either step 596 or step 602 appropriately is negative, this means that the air pressure has not reached the desired pressure and control proceeds to step 560 which causes the microprocessor to iterate the sequence until the pressure is not less than the desired pressure. If the result from the subtractions is non-negative, step 604 transfers control to step 606 which sets VENTFLG and increments PASSCNT. Next, step 608 checks to see if PASSCNT equals five. If it does not, control proceeds to ADJEND sequence 536. If PASSCNT does equal five, control is passed to step 610 which sets LEAKFLG to indicate that there is a probable leak condition in the system. Control then proceeds to step 592 which sounds the appropriate alarm and continues as previously described.

d. VENT Sequence

The VENT sequence 556 (FIG. 13A, 13B) is used when the pressure in tourniquet T or blood pressure cuff B is greater than the desired pressure. The first step in the sequence is step 620 which causes microprocessor 26 to open the vent and turn off the pump. Step 622 then displays the pressure using the DISPRES sequence 700. Control is then passed to step 624 which tests the display count value in DISPCNT. If the value is equal to zero, control passes to step 640. If the value is not equal to zero, control passes to step 626 which checks to see if the current pressure is less than 20 mmHg. If the current pressure is less than 20 mmHg, control is passed to step 640. Otherwise control is passed to step 628 which subtracts the last pressure value from the current pressure value. If the result is non-zero, control is passed to step 640. If the result is zero, control is passed to step 630 which increments alarm counter ALRMCNT. Step 632 then checks to see if the alarm counter has a value of 3. If it does not, control is passed to step 640. If the alarm count does equal 3, step 634 closes the vent and step 636 calls the ALARM sequence 1170 and sounds the appropriate alarm. Upon returning from the ALARM sequence 1170, ALRMFLG is tested. If it is equal to one, control is returned to step 636, therefore forming a loop. If the alarm flag is equal to zero, control is passed to step 640.

Step 640 subtracts the current pressure value from the desired control value. If the result is negative, control returns to step 620 thereby forming the vent loop. If the resultant value is not negative, control passes to step 642 which closes the vent valve 56 because this is the condition where the current pressure has dropped to at least the desired value. After the vent is closed, the current pressure is displayed by step 644 using DISPRES sequence 700 and the power on flag is tested by step 646. If the power on flag is set, step 648 creates a beep and step 650 clears the power on flag. Following step 650 there is a six second delay created by step 652. Had the power on flag been cleared, control would have passed directly to the six second delay of step 652. After the delay is over, the DISPRES sequence 700 is executed by step 654 and control is passed to step 656.

In step 656 the control or desired value is subtracted from the current pressure. If the result is not positive, control is passed to step 660. If the result is positive, control is passed to step 658 which checks to see if the result is less than or equal to five. If the result is less than or equal to five, control is passed to step 660 which clears VENTFLG and proceeds to the ADJEND sequence 536. If the current pressure value is still greater than 5 mmHg from the desired control value, step 658 transfers control to step 620 thereby continuing the vent loop until the desired pressure is reached.

e. ADJEND Sequence

The ADJEND sequence 536 (FIG. 14) is executed each time the necessary pressure adjustments have been completed. The sequence begins with step 670 which causes microprocessor 26 to turn off air pump 64. Next, step 672 resets the vent delay timer to two minutes. Following this, step 674 clears alarm flag ALRMFLG and step 676 uses DISPRES sequence 700 to display the current pressure. The current control or desired value is saved for later use in the CONTLST location by step 678 and control proceeds to step 680.

Step 680 tests the power on flag status. If the power on flag is off, control proceeds to step 690 which is a return from ADJUST sequence 520. If the power on flag is set, step 682 tests DISPFLG. If DISPFLG is set indicating blood pressure is displayed, control also passes to step 690. If the display flag is cleared indicating tourniquet pressure is displayed, step 684 beeps once and step 688 clears the power on flag. Control is then passed to step 690 and the ADJUST sequence 520 is completed.

f. DISPRES Sequence

The DISPRES sequence 700 (FIG. 15) is used to read the current pressure and display it in the appropriate display. The sequence is entered with the pneumatic valves 52–60 in the proper position for reading the desired pressure, either tourniquet T or blood pressure cuff B. The sequence begins at step 702 which uses the RDPRESS sequence 730 to read the current pressure value. The display flag DISPFLG is then tested in step 704 to determine whether the blood pressure cuff pressure or the tourniquet pressure was just read. If the blood pressure cuff B was just read, step 706 displays the blood pressure cuff pressure into the blood pressure display 42, sets the positive blood pressure cuff pressure flag and then passes control to step 718. If the tourniquet pressure was read, step 708 subtracts the current tourniquet pressure reading from the previously displayed tourniquet pressure reading. If the result is negative, the operation is reversed and the previous tourniquet pressure reading is subtracted from the current tourniquet pressure reading in step 710. Step 710 is followed by step 712 which is also where control passes if the current pressure is less than the previous tourniquet pressure as determined in step 708. Three is subtracted from the results of the previous subtraction in step 712. If the result of this further subtraction is zero, control passes to step 718. If the result is negative, step 714 adds the current tourniquet pressure and the previously displayed tourniquet pressure, divides by two and stores the result as the current tourniquet pressure. After this step or if the result from the subtraction in step 712 was positive, step 716 causes microprocessor 26 to store the current tourniquet pressure in the previously displayed tourniquet pressure memory location and display the current tourniquet pressure. Control then passes to step 718.

Step 718 causes microprocessor 26 to determine whether two seconds have elapsed as measured in DISPCNT and if so, the current pressure value is stored in the previous pressure value location in step 720. Thereafter, step 722 causes microprocessor 26 to clear the display count timer and return control from the DISPRES sequence 700 at step 724 which is also where control would have passed if the display counter two second test in step 718 had not equalled two.

g. RDPRESS Sequence

RDPRESS sequence 730 (FIG. 16) is executed by microprocessor 26 to read the pressure in the appropriate cuff. The sequence begins by passing control to the RDAD16X sequence 732. The RDAD16X sequence 732 reads the value held in analog to digital converter 24 sixteen times with a one millisecond delay between samples, and returns an averaged, rounded value of the result. In step 734 the loop counter is prepared and space is cleared for calculations. In step 736 converter 24 is actually read. Step 738 sums the current result of reading the A to D converter 24 to a running total. Step 740 is a one millisecond delay which is followed by step 742 which checks to see if there have been 16 readings yet as set up by the loop counter in step 734. If 16 readings have not been completed, control returns to step 736 and steps 736–742 are re-executed.

If the 16 readings have been completed, control passes to step 744 which causes microprocessor 26 to average the sixteen readings and round the result. This averaged result is saved in step 746 and control is returned to the calling sequence in step 748. Upon returning from the RDAD16X sequence 732, the RDPRESS sequence 730 converts the average voltage result from converter 24 to a corresponding mmHg pressure reading in step 750. Step 752 causes microprocessor 26 to read the status of the display flag to determine if the value just read was a tourniquet value or a blood pressure cuff pressure value. If it was a tourniquet pressure value, step 754 stores the result in the tourniquet pressure register and passes control to step 758. If it was a blood pressure cuff pressure reading, step 756 stores the result in a blood pressure register and transfers control to step 758 which returns control from the RDPRESS sequence 730 to the calling sequence.

h. KINK Sequence

The KINK sequence 760 (FIG. 17) is used to determine if there is a kink in one of the lines to either blood pressure cuff B or tourniquet T. After entry, KINK sequence 760 begins executing at step 762, which causes microprocessor 26 to execute the RDPRESS sequence 730 to determine the pressure in the sense side of the desired pressure line. Step 762 also causes the result of this reading to be displayed in tourniquet pressure display 46. Step 764 changes the setting of the valves to read pump line 94 and transfer control to step 766 which causes microprocessor 26 to execute RDPRESS sequence 730 to read the pressure of pump line 94. Step 768 subtracts the sense side reading from the pump side reading. The allowable difference of 4 mmHg is subtracted from this value. If the resultant value is positive, this indicates a kink and step 770 causes microprocessor 26 to issue the appropriate alarm by executing ALARM sequence 1170. Control is then transferred to step 772. If the result of the subtractions of step 768 is negative, this indicates that the pressures between the two portions of the line are within allowable limits and that there is no kink. Control then passes to step 772 which resets valves 52–60 to the sense side and step 774 returns control to the calling sequence.

2. Automatic Mode

Automatic mode is the preferred mode of operation of the apparatus A. In this mode of operation the device automatically reads the patient's systolic blood pressure using the blood pressure cuff B and maintains the tourniquet pressure at a level slightly above systolic blood pressure as prescribed by the operator via the value set in control display 48.

Figure 18A:
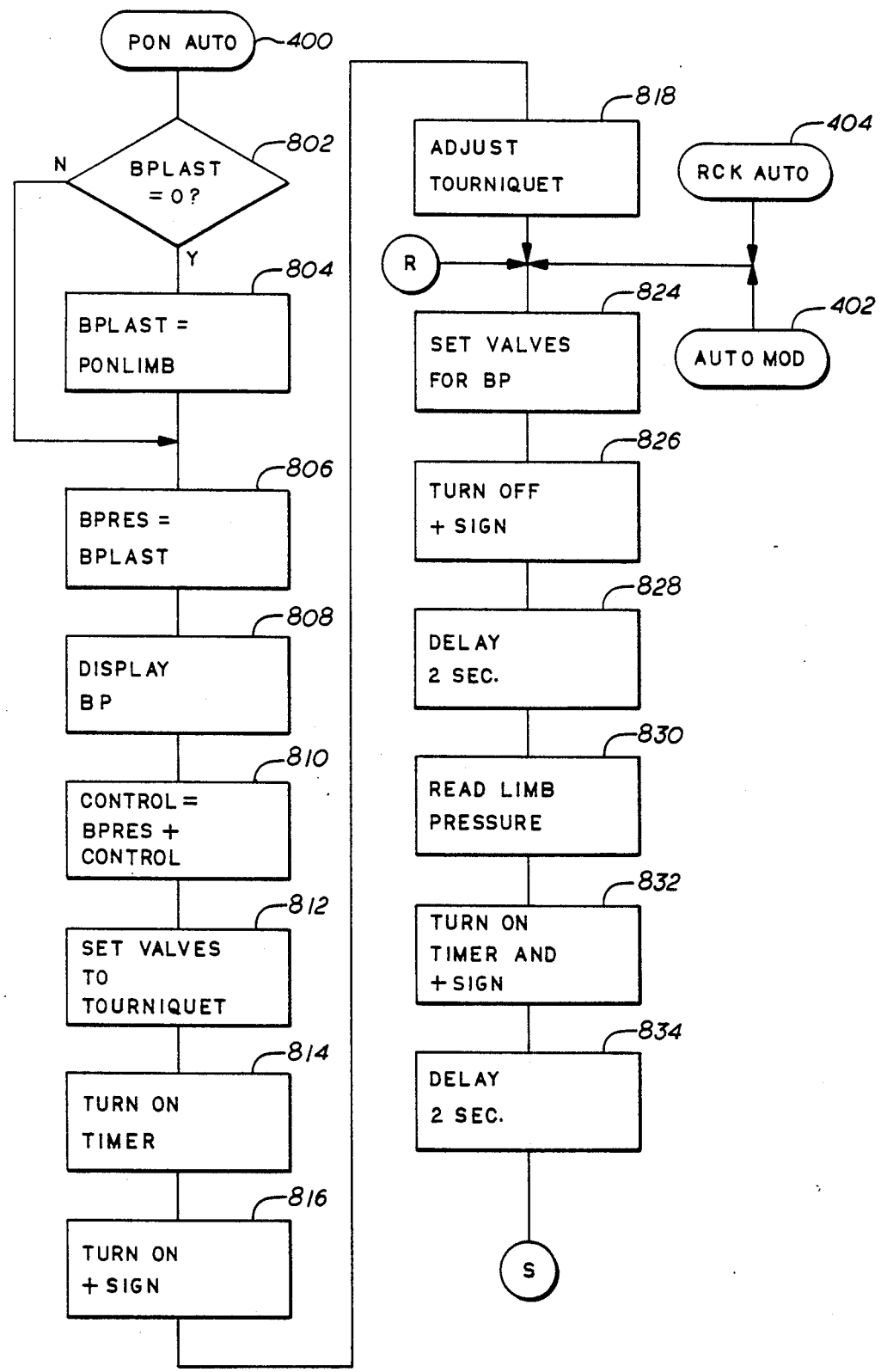
Figures 18B, 20A:
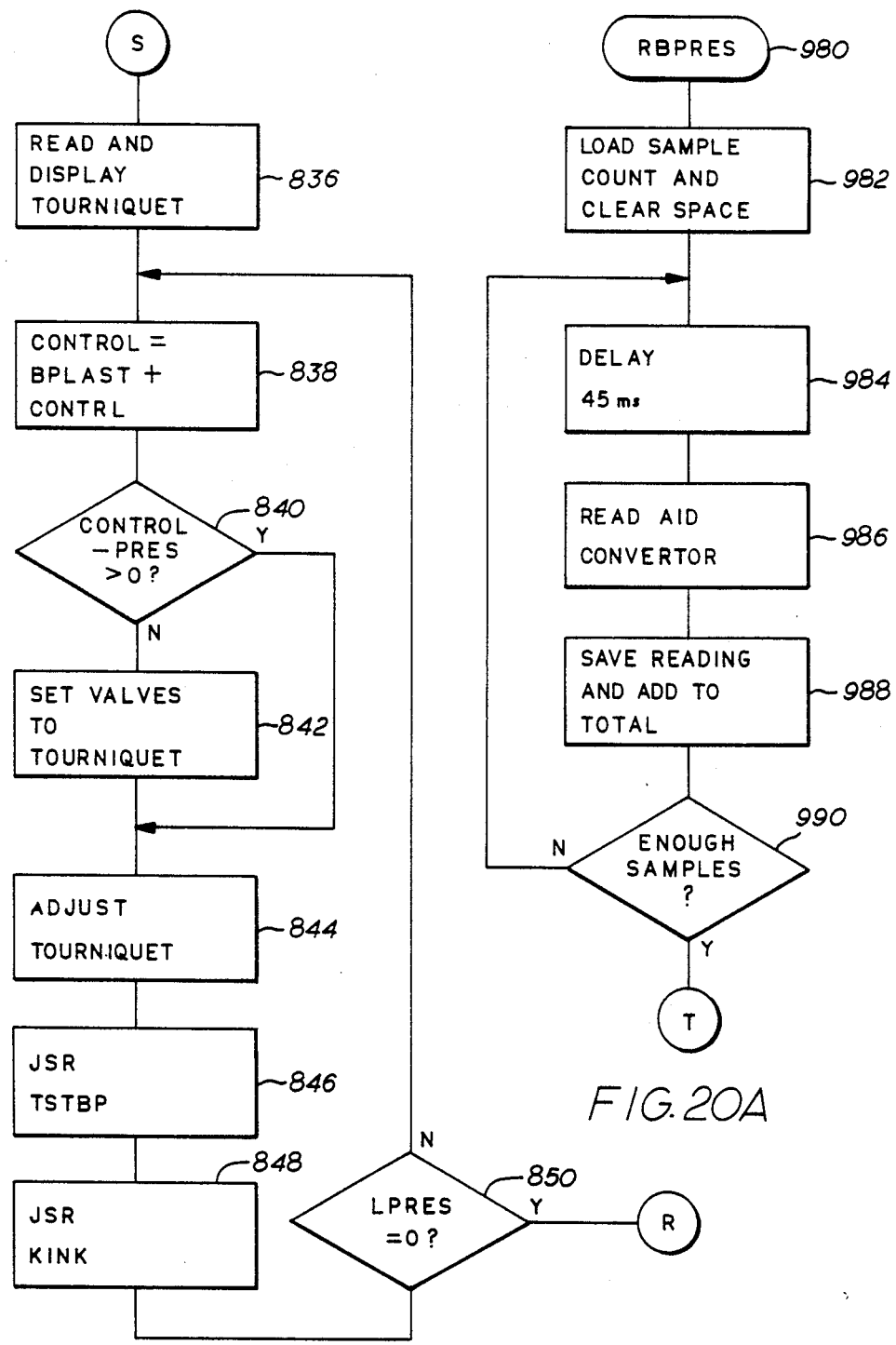
Figure 19A:
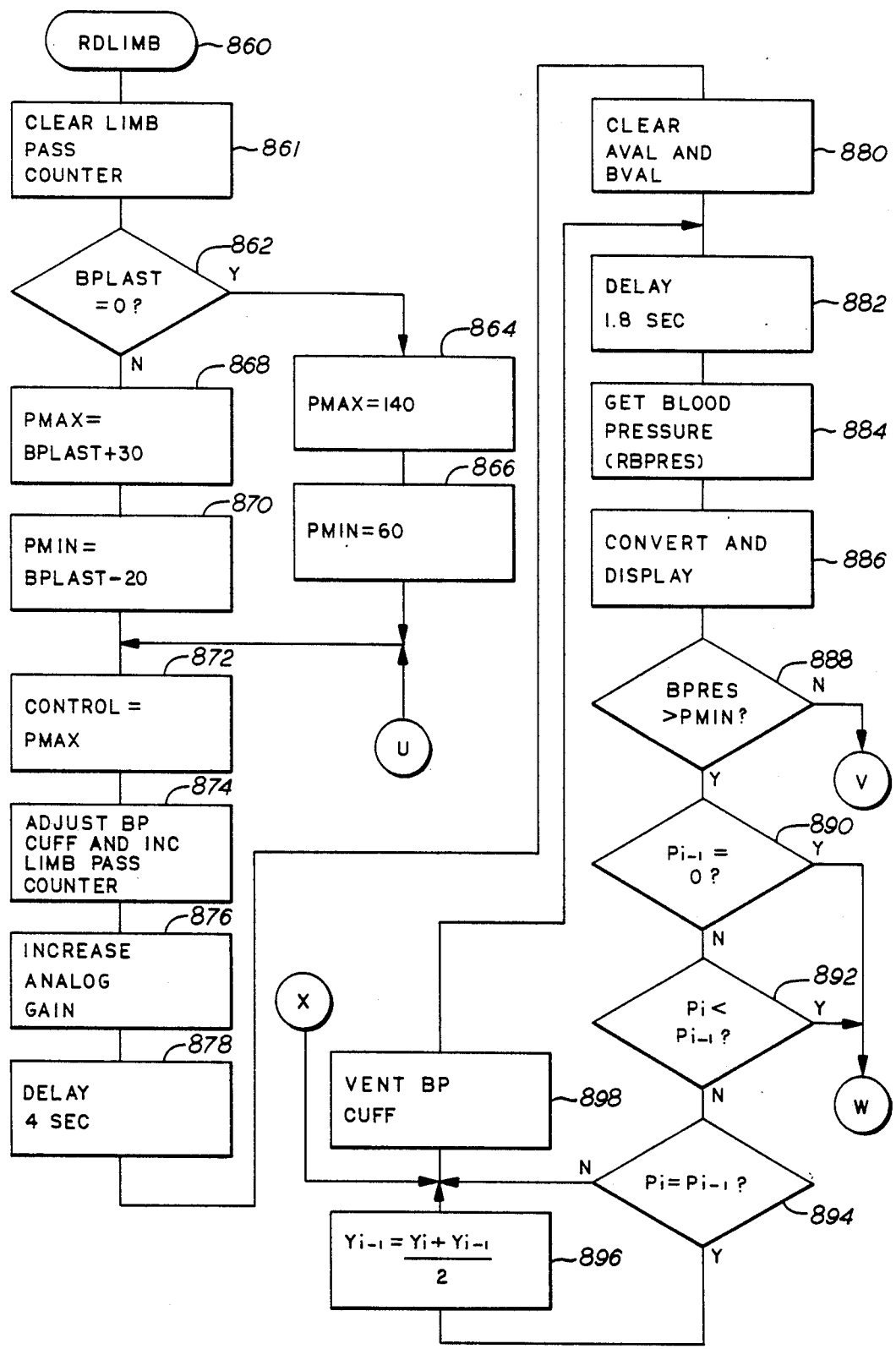
Figure 19B:
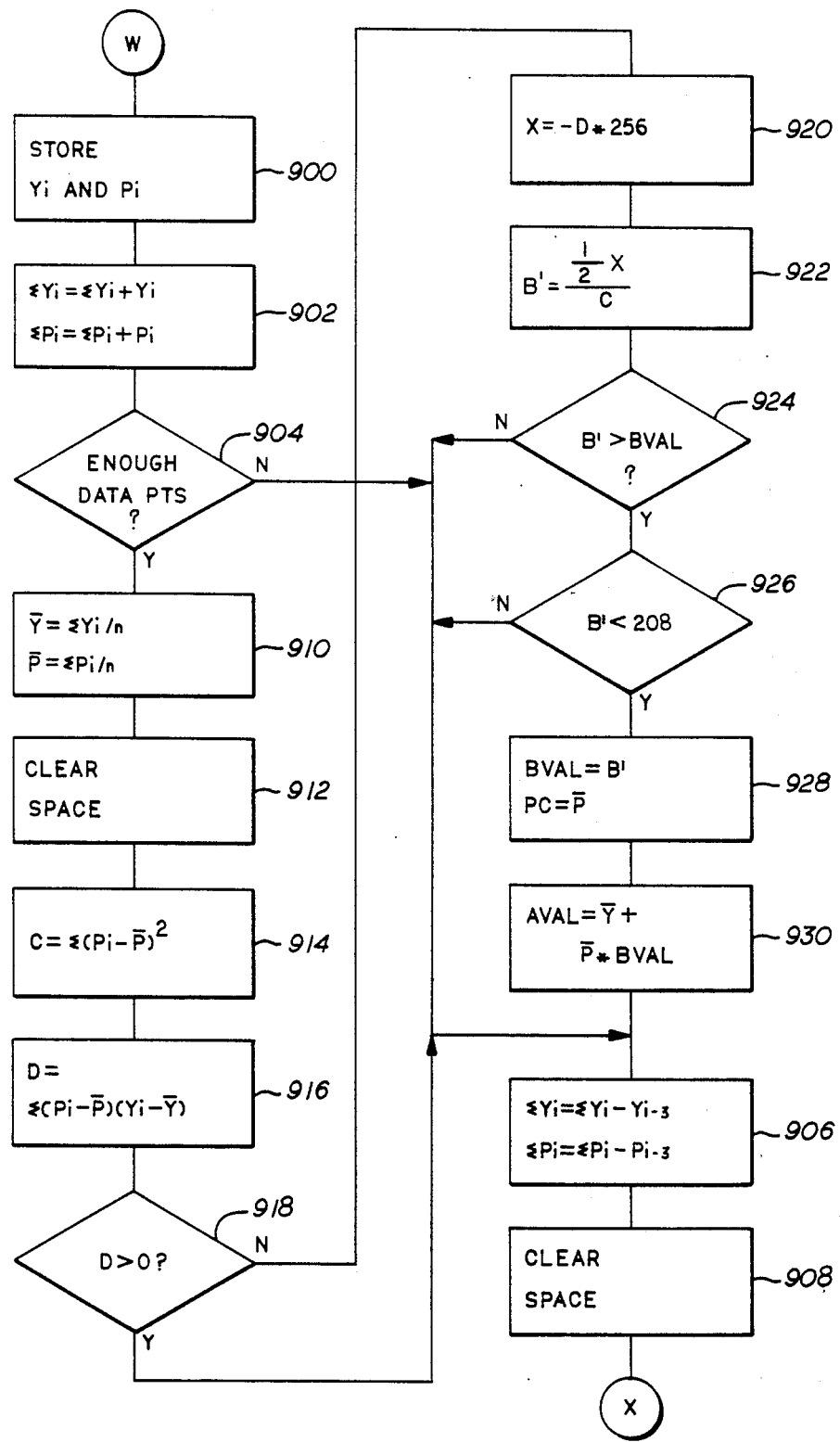
Figure 19C:
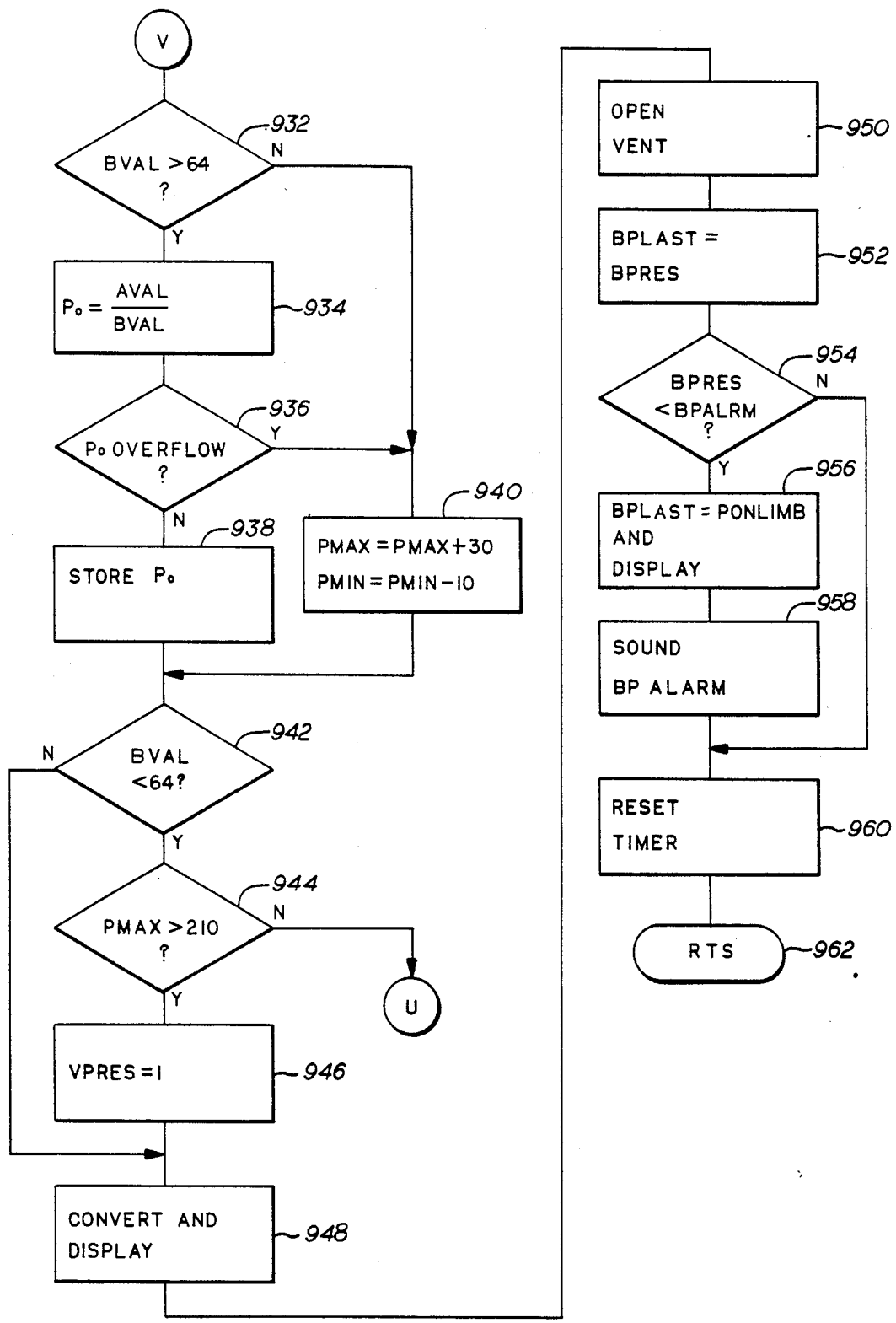
Figure 20B:
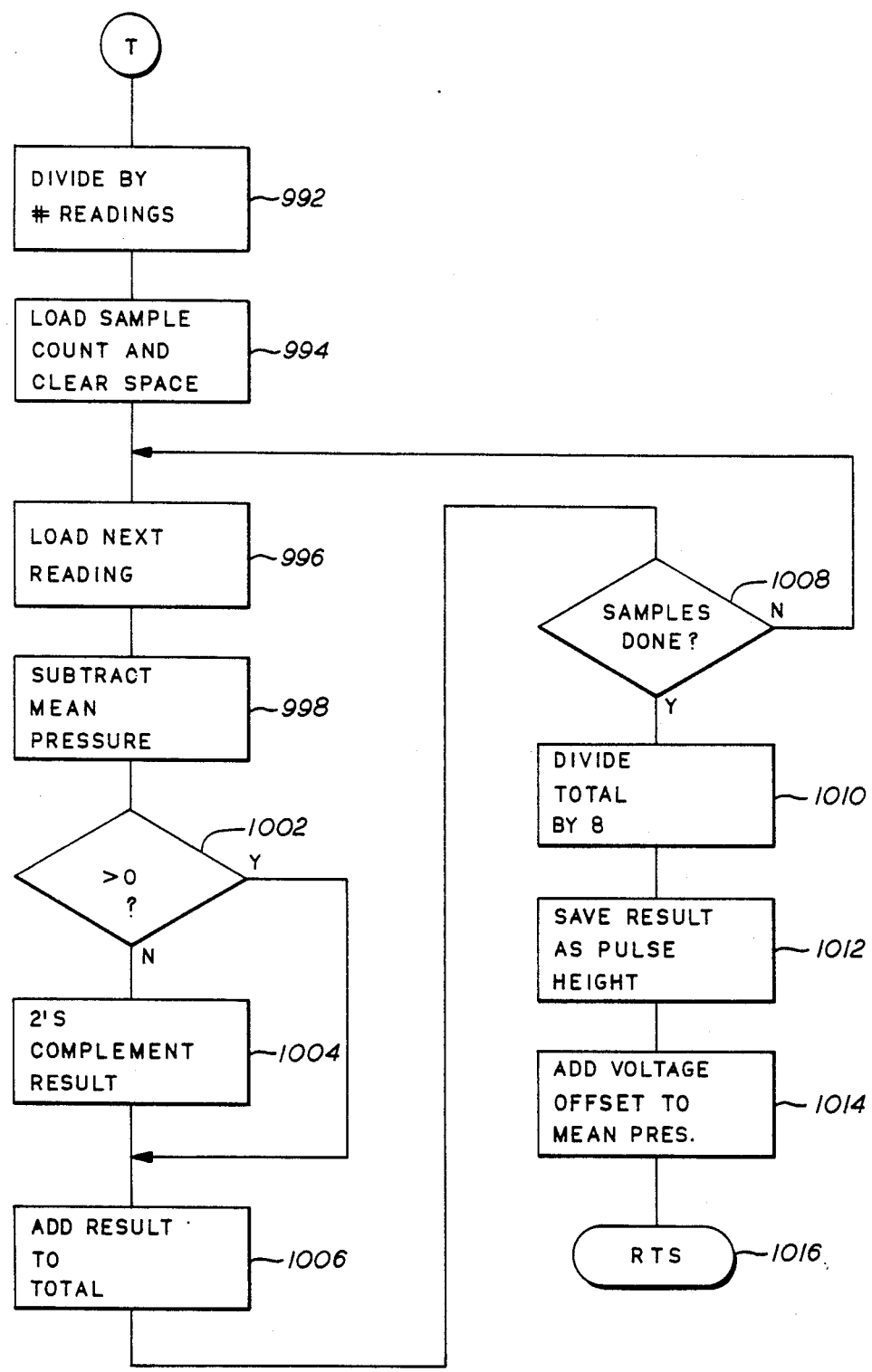

Referring now to FIGS. 18A, 18B, there are three ways to enter the automatic mode. The first is the PONAUTO sequence 400. This occurs if mode switch 68 is in the automatic position when the power is turned on. The second entry to the sequence is the RCKAUTO sequence 404. This sequence is used to initiate a blood pressure reading and resulting tourniquet correction on command in response to actuation of recheck switch 76. The third path is the AUTOMOD sequence 402. This is achieved when the apparatus has been turned on and mode switch 68 is transferred from the off position to the automatic position. With switch 68 in thi automatic position and recheck switch 76 off, a systolic blood pressure reading is taken and tourniquet control value pressure is updated on two minute intervals with more frequent updates occurring using the RCKAUTO sequence 404.

a. PONAUTO Sequence

As seen in FIG. 18A, the PONAUTO sequence 400 be executing at step 802 which causes microprocessor 6 to determine if the previous blood pressure reading was equal to zero. If it was, step 804 sets the previous blood pressure reading to the initialized or power on limb pressure value of 180 mmHg. Control then proceeds to step 806 which is also where control would have proceeded if the previous blood pressure reading had not been zero. Step 806 sets the value of current blood pressure reading variable equal to the previous blood pressure reading. This current blood pressure reading is then displayed in step 808. Step 810 causes microprocessor 26 to add the desired tourniquet pressure differential to the current blood pressure value and stores this as the control value. The pneumatic valves 52-60 are then set for tourniquet operation in step 812. The elapsed time timer is turned on in step 814. Step 816 turns on the plus sign which is used to indicate to the operator that the controller C is in automatic mode and is adjusting the tourniquet to the systolic blood pressure reading plus the desired differential setting. Step 818 causes microprocessor 26 to execute ADJUST sequence 520 to adjust the tourniquet pressure to the control value. Control then proceeds to step 824.

RCKAUTO Sequence 404 and AUTOMOD sequence 402 both start with step 824. The reason for two entry points into this step is that the automatic sequence eventually forms a closed loop and RCKAUTO sequence 404 entry is needed to update the limb pressure reading more frequently than the loop allows. The AUTOMOD sequence 402 entry is an initial entry point for the routine from other operating modes.

Step 824 causes microprocessor 26 to set pneumatic valves 52-60 to allow inflation or deflation of blood pressure cuff B. The plus sign is turned off in step 826 to indicate that the apparatus is not actively controlling the tourniquet pressure because a blood pressure reading sequence is being initiated. There is a two second delay created by step 828 at which time step 830 passes control to the RDLIMB sequence 860 that reads the limb pressure. After the limb systolic blood pressure has been determined, control returns to step 832 which activates the tourniquet elapsed timer and turns on the plus sign indicating active control has resumed. Control is transferred to step 834 which provides a two second delay whereafter tourniquet pressure is read and displayed in step 836.

Step 838 causes microprocessor 26 to determine a new tourniquet control value by first adding the previous blood pressure reading to the desired incremental pressure, and thereafter, in step 840 subtracting the current tourniquet pressure reading from the control value. If the result is negative this indicates that the tourniquet pressure is too high and step 842 sets the pneumatic valves 52-60 for tourniquet operation. Control then passes to step 844. If the result of the control value minus the current pressure subtraction is positive this indicates that the tourniquet pressure is insufficient and control proceeds to step 844. Step 844 causes microprocessor 26 to execute ADJUST sequence 520 to adjust the tourniquet pressure to the desired control pressure.

Upon returning from ADJUST sequence 520, control proceeds to step 846 which causes microprocessor 26 to execute TSTBP sequence 1070 to vent blood pressure cuff B. Next, step 848 causes KINK sequence 860 to be executed to determine if there is a kink in the tourniquet line. At step 850 microprocessor 26 reads the two-minute timer LPRES to determine whether it is time to reinitiate a blood pressure reading. If it is not time to reinitiate a blood pressure reading, control is passed to step 838 and the controller C proceeds in the tourniquet control loop. If it is time to recheck the blood pressure, control is passed to step 824 and the AUTOMOD sequence 402 is executed again. Thus, if no change occurs in the status of the operator actuated front panel switches, controller C operates in a closed loop, regularly and automatically monitoring and maintaining tourniquet cuff pressure.

b. Systolic Blood Pressure Calculation i. Theoretical Basis

Figure 6:
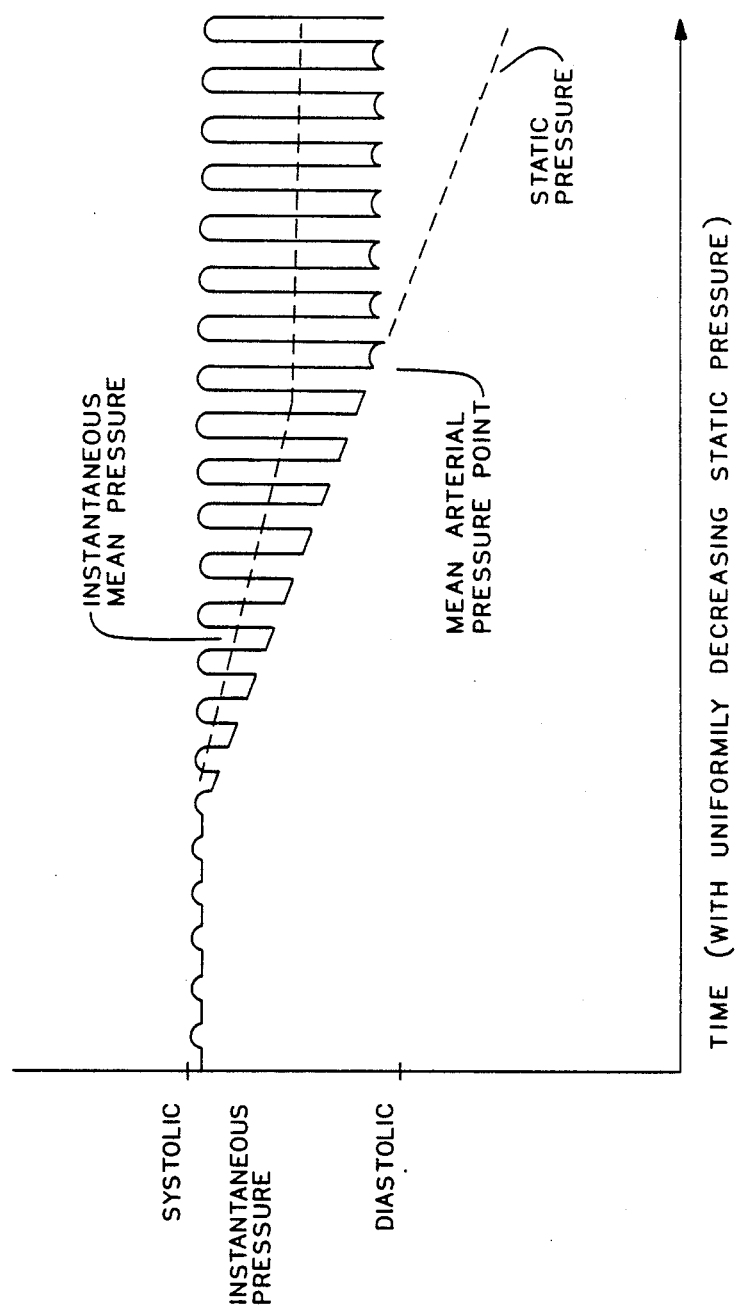
FIG. 6 is a graph of the instantaneous pressure on the blood pressure cuff as the air pressure in the cuff is reduced.

RDLIMB sequence 860 (FIGS. 19A, 19B, 19C) is the main sequence used by microprocessor 26 to read the patient's systolic blood pressure. This is done by calculating the equation of a straight line between a number of points of blood pressure cuff pressure and blood pressure pulse height. At a given pressure in the cuff the blood pressure will exert a pulse of a given height. This relationship is shown in FIG. 6. As can be seen in the figure, as the pressure in the cuff B is increased, the height of the pulse decreases over the static pressure in the cuff B. The point at which the pulse is reduced to a very small constant level is the systolic blood pressure. Therefore, using the equation of a straight line and setting the pulse height to zero, the systolic blood pressure can be computed from the slope and intercept as shown.

$$y = a + bp$$

$$o = a + bp$$

$$p = -a/b$$

where
 $y$ = pulse height
 $p$ = blood pressure.

Therefore, it is necessary to determine the values of the slope and intercept for the equation of this line for the patient. This is done by taking a number of samples at a number of different static blood pressure cuff pressures and using a least squares fit solution to determine the values. The basic equation to be solved is:

$$y = a + bp$$

which becomes $$na + b\Sigma p_i = \Sigma y_i$$

$$a\Sigma p_i = b\Sigma p_i^2 = \Sigma p_i y_i$$

where
 $y_1$ = pulse height
 $p_i = p_1$
 $n$ = number of samples by using a least squares transformation. Solving the least square equations for the slope and intercept values gives the following equations.

$$b = \frac{n\Sigma p_i y_i - (\Sigma p_i)(\Sigma y_i)}{n\Sigma p_i^2 - (\Sigma p_i)^2}$$

$$a = \bar{y} - b\bar{p}$$

where
 $\bar{y} = \Sigma y_i/n$
 $\bar{p} = \Sigma p_i/n$

These equations are not in an optimal form for microprocessor use and therefore by transformation the following equations are obtained.

$$b = \frac{\Sigma(p_i - \bar{p})(y_i - \bar{y})}{\Sigma(p_i - \bar{p})^2}$$

$$a = \bar{y} - b\bar{p}$$

The method of the present invention includes three error reducing means to insure better accuracy of the slope and intercept values as calculated. The first technique is an averaging technique applied to a number of instantaneous cuff pressure readings to determine the pulse height. A second check is to insure that the slope of the line is within given acceptable, possible values. The final check is to see if the calculated blood pressure is within reasonable and obtainable bounds.

ii. RDLIMB Sequence

The RDLIMB sequence 860 is the main sequence that microprocessor 26 executes to read limb systolic blood pressure. The sequence begins at step 861 which clears the limb pass counter. Step 862 tests to see if a previous blood pressure was found. If a previous blood pressure was not found, step 864 sets the value of maximum pressure variable to 140 mmHg and step 866 sets the minimum pressure variable to 60 mmHg. Control then proceeds to step 872. If a blood pressure had been previously found, step 868 sets the value of maximum pressure variable to 30 mmHg greater than the previously read blood pressure value and step 870 sets the minimum pressure value to 20 mmHg less than the previous blood pressure value. Control then proceeds to step 872 which sets the CONTROL value equal to the maximum pressure value. Step 874 increments the limb pass counter and causes microprocessor 26 to execute ADJUST sequence 520 to set the blood pressure cuff pressure at the desired maximum pressure as contained in CONTROL. Step 876 causes microprocessor 26 to provide a gain control signal to alter the gain of the input analog signal to analog to digital converter 24 to allow greater resolution of the signal at lower signal voltages. Step 878 delays four seconds and then step 880 clears memory space for the slope (BVAL) and intercept (AVAL) values which will be determined. Step 882 causes a to 1.8 second delay and then passes control to step 884. Step 884 calls the RBPRES sequence 980 which causes microprocessor 26 to sample the blood pressure cuff pressure and return the average value of the pressure and the pulse amplitude.

The RBPRES sequence 980 (FIGS. 20A, 20B) performs the first filtering or averaging of the data samples used in the present invention. The routine calculates the pulse height of a blood pressure pulse by determining the mean deviation of a number of samples and multiplying this result by 4. This multiplication is done to increase the accuracy of future calculations. It is merely a scale factor that disappears when the straight line equation is solved for the zero pulse height point. The basic equation is shown below.

$$y_i = \frac{4}{n} \Sigma |p_{1i} - \bar{p}_1|$$

where $\bar{p}_1 = \Sigma p_{1i}/n$ $p_{1i}$=instantaneous pressure reading at one blood pressure cuff static pressure $y_i$=pulse height n=number of samples.

RBPRES sequence 980 begins executing at step 982 by loading a sample count of 32 and clearing the necessary space for the calculations. There is a 45 millisecond delay in step 984 after which time analog to digital converter 24 voltage is read in step 986. Step 988 saves this instantaneous pressure value and adds this to a running total. If the 32 samples have not been completed, step 990 transfers control to step 984 and another sample loop is executed. If all 32 samples have been taken, step 990 transfers control to step 992 which divides the running total by 32 to obtain a mean value of the instantaneous rea Step 994 loads the sample count of 32 and clears space for another new running total. Step 996 loads an instantaneous reading and step 998 subtracts the mean value of the instantaneous readings from this individual reading. If the result is positive, control is transferred directly to step 1006. If the result from the subtraction is negative, step 1002 transfers control to step 1004 which performs a two's complement on the result of the subtraction thereby performing an absolute value.

The absolute value of the subtraction is added to a running total in step 1006 and then step 1008 determines if all the samples have been added to the total. If all samples have not been added to the total, control is transferred back to step 996 and another instantaneous reading is used. If all the samples have been completed, step 1010 divides the running total by 8. This operation is actually dividing the running total by 32 thereby producing the mean deviation of the sample and then multiplying this result by the scale factor of 4. By dividing by eight instead of dividing by 32 and multiplying by four, more significant digits are retained for better accuracy. The result from step 1010 is saved as the sample pulse height at that tourniquet pressure in step 1012. Step 1014 loads the mean of the instantaneous pressure readings and adds the voltage offset correction value and stores this value. Step 1016 then returns control to the calling sequence.

Control is returned to the RDLIMB sequence 860 to step 886. Step 886 displays the mean instantaneous pressure value calculated in the RBPRES sequence 980 in the blood pressure display 42. Next, step 888 checks to see if this mean instantaneous blood pressure is greater than the minimal blood pressure previously set. If it is not greater, control proceeds to step 932. If the pressure is greater than the minimum pressure, step 890 checks to see if the previous pressure value was zero. If it was, control passes to step 900. If the previous pressure value was not zero, step 892 checks to see if the current pressure reading is less than the previous pressure reading. This is a condition that is true when the blood pressure cuff pressure is between actual systolic pressure and the mean arterial pressure. This is the second means of insuring that the data points to be used in calculating the blood pressure are correct. This check insures that the data values are for the systolic-to-mean arterial pressure region and not for the other possible regions. If the current pressure is less, control is transferred to step 900. If the current instantaneous mean pressure is not less than the previous instantaneous mean pressure, step 894 checks to see if the two pressures are equal. If they are not equal, control passes to step 898. If they are equal, control passes to step 896.

Step 896 removes the previous pulse amplitude value from the running pulse amplitude sum and averages the previous and present pulse amplitude values. This average result is then added back into the running pulse amplitude sum and control is passed to step 898. Step 898 vents the blood pressure cuff for a time period that is inversely proportional to the pressure in the blood pressure cuff B. The inverse proportion is necessary because at a higher pressure air will flow out faster and therefore less time is required to decrease the pressure by approximately equal amount. Control is then passed to step 882 to form a loop.

If it has been determined that a pressure value is of a suitable slope by steps 890 or 892, step 900 stores the pulse height and instantaneous mean pressure value of that data point. In step 902 the current data point's pulse height and pressure values are added to the running totals for pulse height and pressure. Step 904 checks to see if enough data points have been obtained to calculate the equation. If enough data points have not been collected, control passes to step 906 which removes the oldest pulse height and pressure values from the running sums and decrements the loop counter to allow room for a new data point. In the case where there were not enough data points, zero values would be removed. Step 908 then clears out the space necessary to store new data points and control proceeds to step 898.

If there were enough data points in step 904, step 910 divides the running pulse height total by the number of data points to produce the mean pulse height and divides the running total of pressures by the number of samples to produce the mean pressure. Step 912 clears space for the calculations that are to follow. Step 914 calculates a variable C which is the sum of the square of the difference between the individual pressures of the data points less the mean pressure. Step 916 computes a variable called D which is the sum of the product of the instantaneous pressure values minus the mean pressure and the pulse height values minus the mean pulse height. This value is checked in step 918 to see if it is greater than zero. This is another check to make sure the data points have a decreasing instantaneous mean pressure and an increasing pulse height. If it is greater than zero, control proceeds to step 906. If it is not greater than zero, step 920 performs a two's complement on the result and multiplies it by 256 and stores the result as the variable X. Control is then passed to step 922 which calculates the value of the variabl B' which is the value of the variable X divided by 2 and divided by the value C which had been previously determined. The division by 2 is necessary to recover accuracy lost by the use of signed numbers in the previous steps. Step 924 then checks the B' value to see if it is greater than BVAL, the previous slope value. If it is not greater, control is transferred to step 906. If it is greater, control is transferred to step 926 which checks to see if the B' value is less than the maximum allowable slope of 208. the value is not less than the maximum allowable slope, control is passed to step 906. This is a third check to make sure the slope of the data points is a possible physiological condition. If the value is less than the maximum slope, control is passed to step 928. In step 928 BVAL is given the current value of B' and the mean pressure value is stored. Step 930 then calculates AVAL by multiplying BVAL by the mean pressure and adding the mean pulse height. Control is then transferred to step 906. Step 906 subtracts one from the loop counter so that the next pressure data point set that meets the initial slope criteria will force a recalculation of the loop. Loop 906 also removes the oldest data point from running totals of pressure and pulse height. Step 908 moves the data point values around to allow space for the next set. Step 908 transfers control to step 898 and a loop is formed. The values of the equation are now calculated and can be used to determine the actual systolic blood pressure of the patient.

After the instantaneous mean pressure has been reduced below the minimum pressure value previously set, step 888 transfers control to step 932. Step 932 checks to see if BVAL is greater than a certain minimum value. This value is currently 64. If it is not, control is transferred to step 940. This condition indicates insufficient variance in sample pulse heights to allow a reliable systolic blood pressure determination. If BVAL is greater than the fixed amount, control is transferred to step 934 which calculates the systolic blood pressure by dividing AVAL by BVAL. Step 936 checks to see if the resultant systolic blood pressure has overflowed the registers. If it has, control is transferred to step 940 which increases the maximum pressure value by 30 and decreases the minimum pressure by 10. Step 940 then proceeds to step 942.

If the systolic blood pressure value did not cause an overflow, step 938 stores the value and transfers control to step 942. Step 942 checks to see if BVAL is less than the minimum fixed amount from before. If it is less than the minimum amount, step 944 checks the maximum pressure value. If this value is not greater than the desired maximum which is currently 210, control is transferred to step 872 and another attempt is made to read the blood pressure. If the maximum pressure value is greater than the maximum allowable value of 210 mmHg, the pressure is set to 1 mmHg by step 946 and control is transferred to step 948.

Step 948 is also where control would go if the BVAL was equal to or exceeded the minimum amount as tested in step 942. Step 948 displays the blood pressure calculated and control proceeds to step 950 which vents the blood pressure cuff. Step 952 then causes microprocessor 26 to save the current blood pressure reading as the previous blood pressure reading and passes control to step 954 which tests to see if the blood pressure value is less than the preset blood pressure alarm value of 70 mmHg. If it is less, this indicates that the patient's blood pressure is below the desired level as preset and control passes to step 956. Step 956 saves the power on limb pressure value of 180 mmHg as the previous blood pressure value and displays this value in the blood pressure display. Step 958 then causes microprocessor 26 to sound the blood pressure alarm and transfers control to step 960. If the blood pressure was greater than the alarm blood pressure in step 954, control transfers directly to step 960 which resets the blood pressure interval frequency timer and returns control to the calling routine via step 962.

3. Off Mode a. OFFMODE Sequence

The third mode of operation of the controller C is the off mode. In this mode there is no checking of the blood pressure and no active control of the tourniquet. The OFFMODE sequence 394 (FIG. 21) begins with step 1040. In step 1040 the previously calculated blood pressure is displayed. Step 1042 then delays two seconds and the tourniquet pressure is determined and displayed by using the DISPRES sequence 700 in step 1044. After returning from displaying the tourniquet pressure, step 1046 causes microprocessor 26 to execute the TSTBP sequence 1070 to make sure the blood pressure cuff is vented. There is then a 100 millisecond delay in step 1048 and control is passed to step 1060. Step 1060 causes microprocessor 26 to read the recheck flag. If the flag is set, control is passed to step 1062. If the recheck flag is not set, control returns to step 1044, thereby forming a closed loop that continuously displays the current tourniquet pressure. In a simple off mode situation, control would stay in this loop.

b. RCHKOFF Sequence

Figure 21:
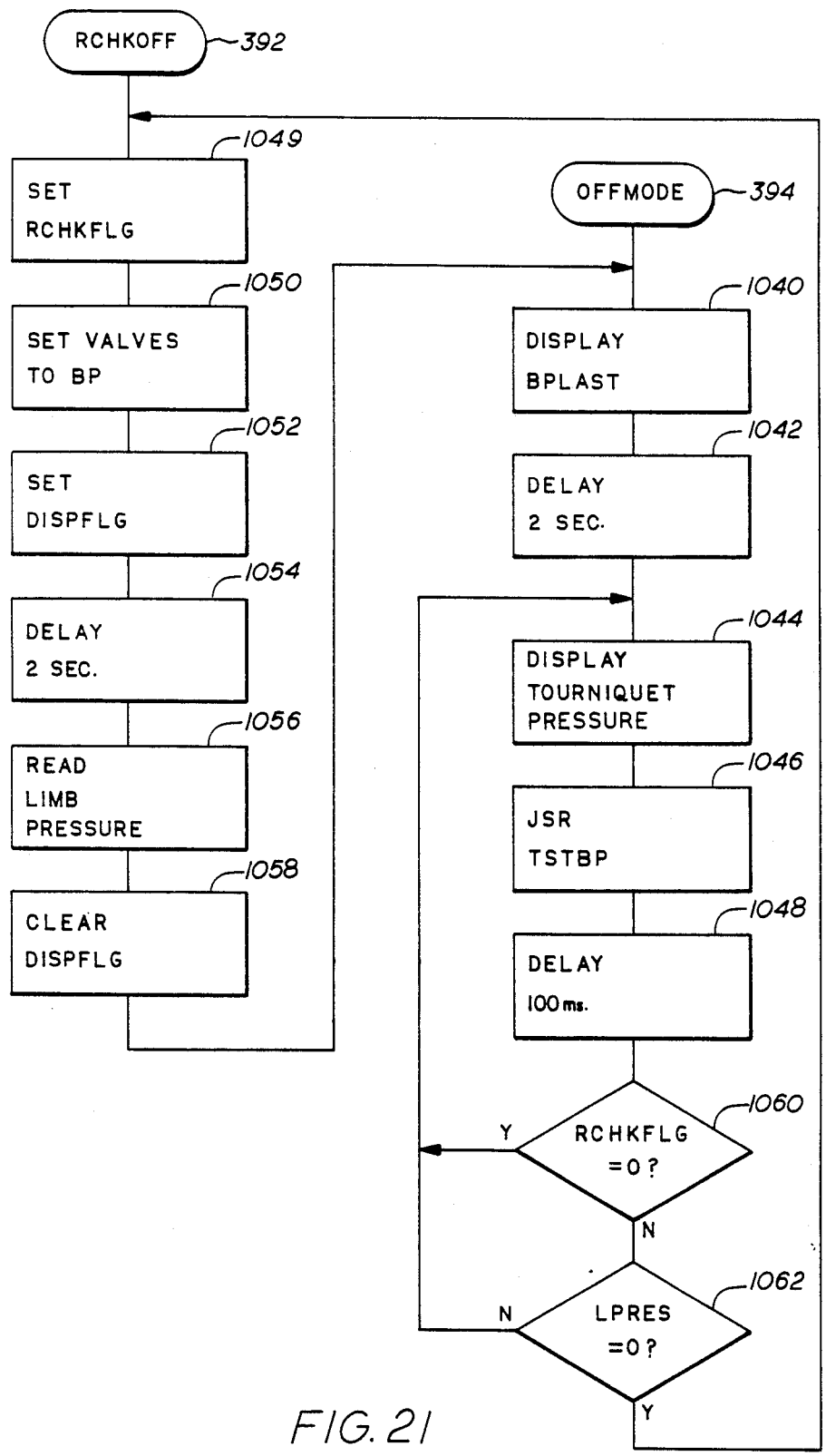

An alternate entry into the OFFMODE sequence 394 is the RCHKOFF sequence 392 (FIG. 21). This entry point is used if mode switch 68 is in the off position and the recheck switch 76 is activated. RCHKOFF sequence 392 begins with step 1049 which sets the recheck flag. Step 1050 the causes microprocessor 26 to set pneumatic valves 52–60 for blood pressure measurement. The display flag is set to the blood pressure pointer in step 1052. A two second delay is created by step 1054. Step 1056 causes microprocessor 26 to execute RDLIMB sequence 860 to read and determine the limb systolic blood pressure. After returning from the RDLIMB sequence 860, the display flag is cleared to indicate tourniquet operation in step 1058 and control is passed to step 1040 whereupon standard OFFMODE control occurs until step 1060 is reached. In this case step 1060 would transfer control to step 1062 because the recheck flag would be set. Step 1062 causes microprocessor 26 to determine whether the required time has passed to initiate an automatic reading of the systolic blood pressure. If enough time has not passed, control returns to step 1044 forming a loop. If it is time to read the systolic blood pressure, control transfers to step 1049 and the RCHKOFF sequence 392 is performed again.

c. TSTBP Sequence

The TSTBP sequence 1070 (FIG. 22) is used to make sure blood pressure cuff B is vented. The sequence begins with step 1072 which causes microprocessor 26 to determine if the positive blood pressure cuff pressure flag has been set. If it has not been set, control proceeds directly to step 1084. If the flag has been set, step 1074 sets pneumatic valves 52–60 to the correct position to vent the blood pressure cuff. Step 1076 then causes microprocessor 26 to execute DISPRES sequence 700 to read the tourniquet pressure and then delays 20 seconds. The positive blood pressure cuff pressure flag is then cleared in step 1078 and pneumatic valves 52–60 are returned to the tourniquet position in step 1080. After a two second delay in step 1082, control is returned to the calling sequence via step 1084.

4. Release

Figure 23:
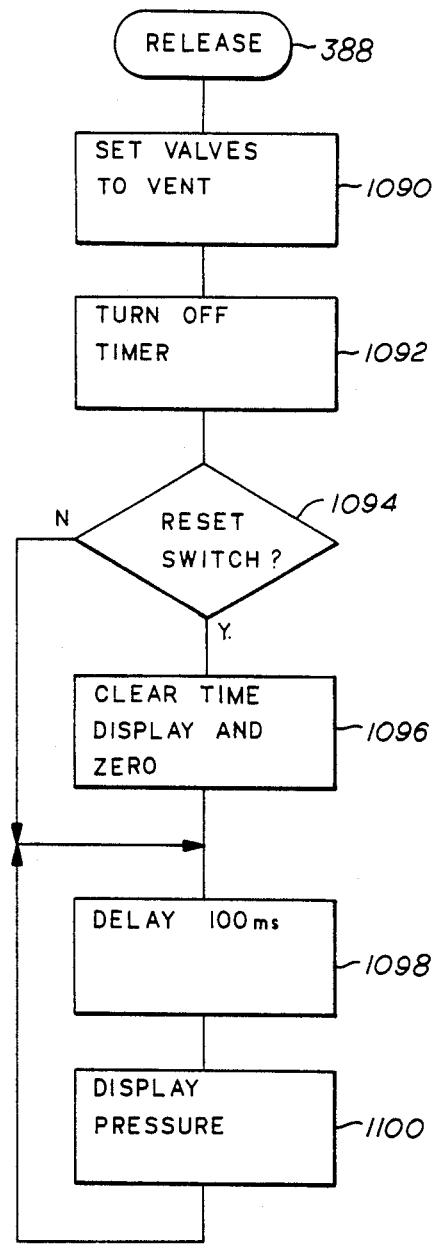
Figure 8:
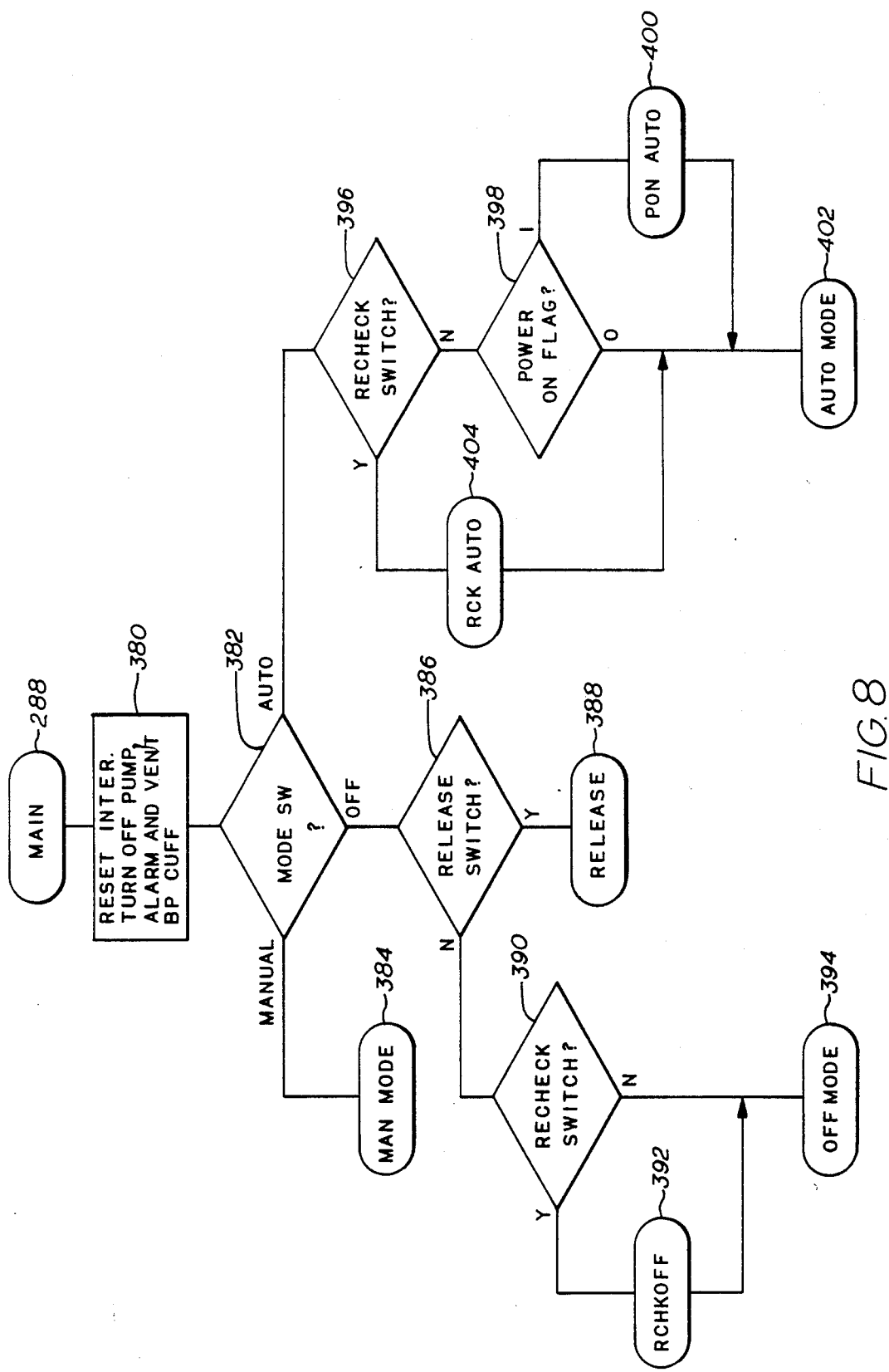
Figure 9A:
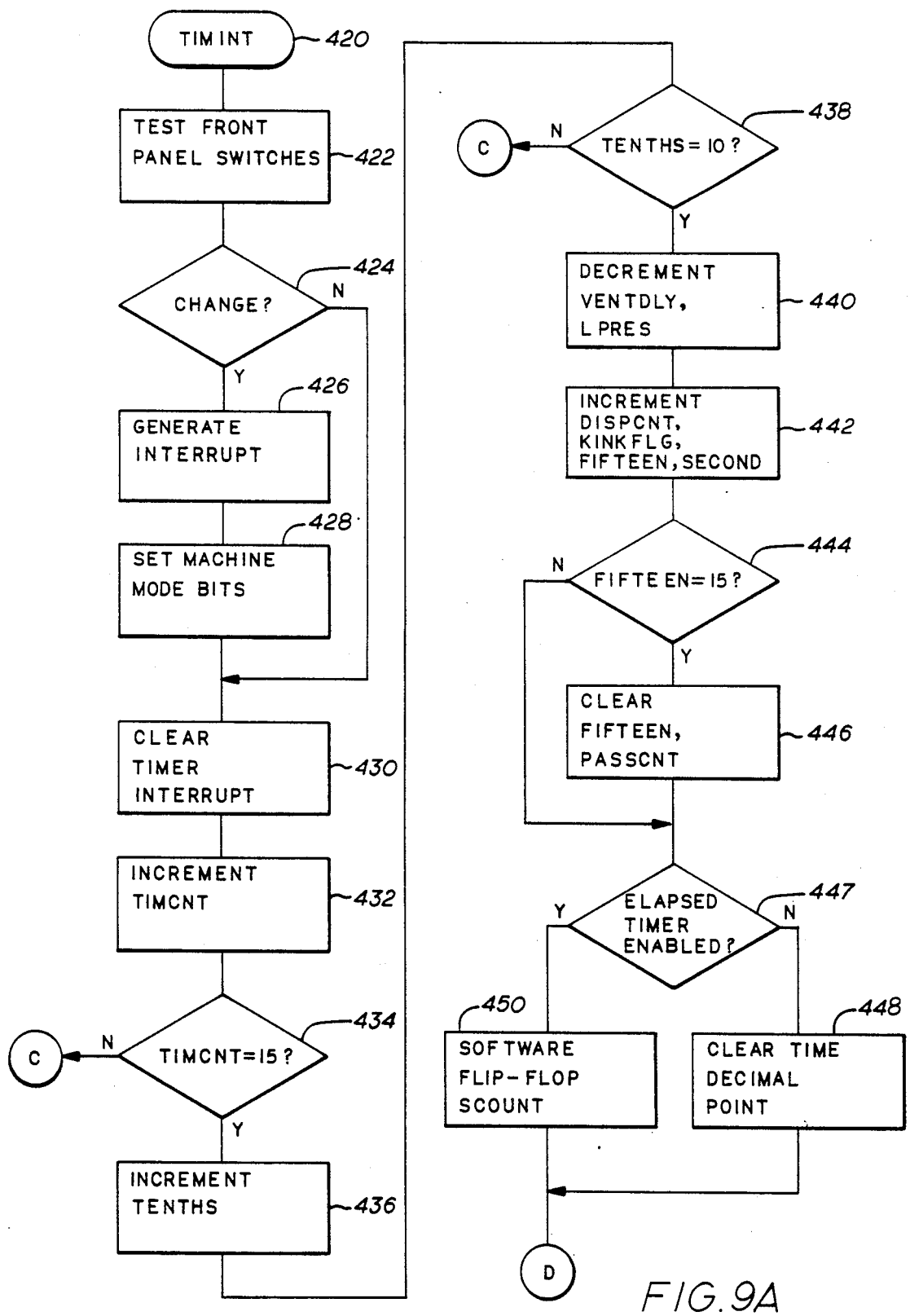
Figure 9B:
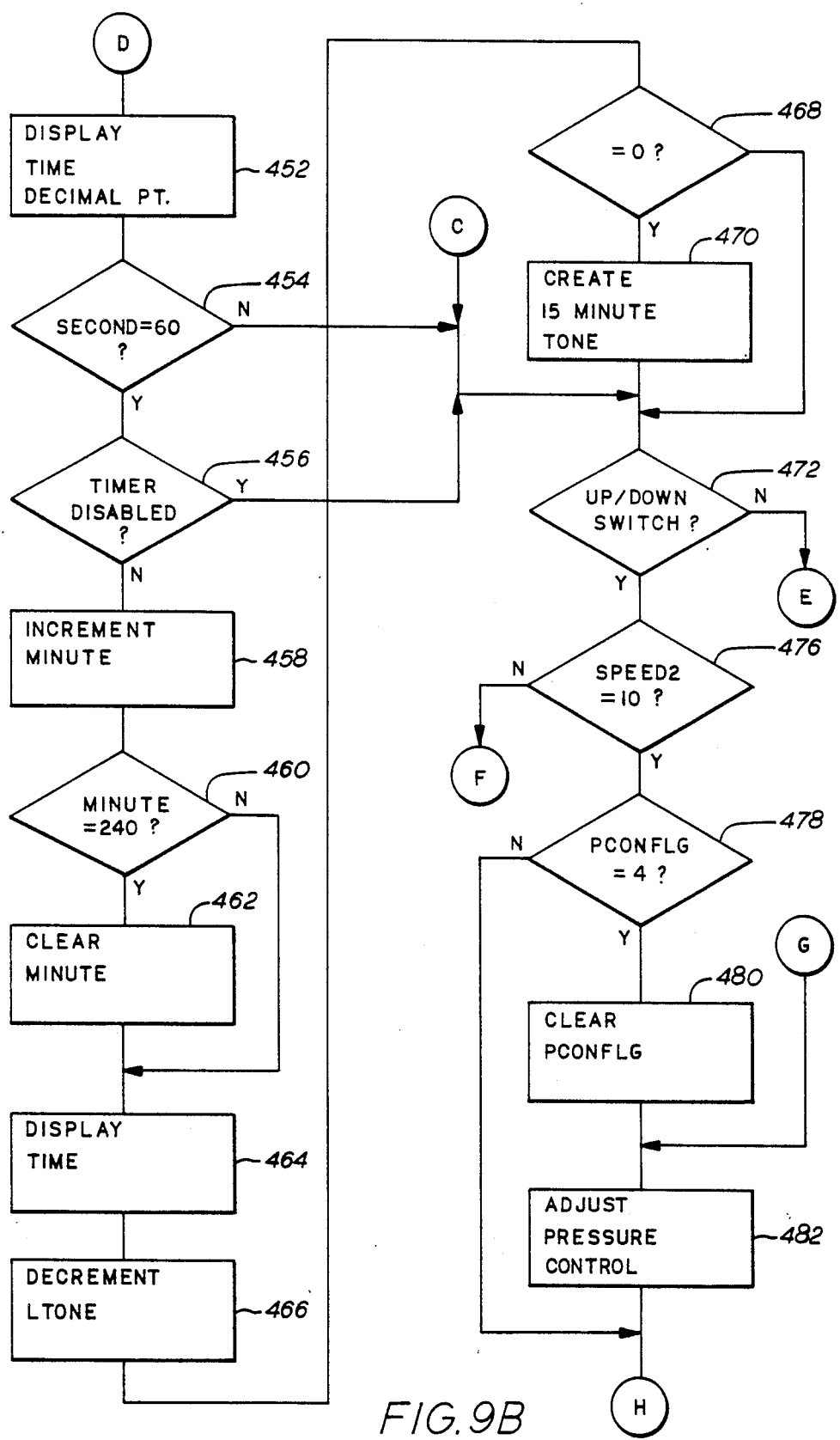
Figure 9C:
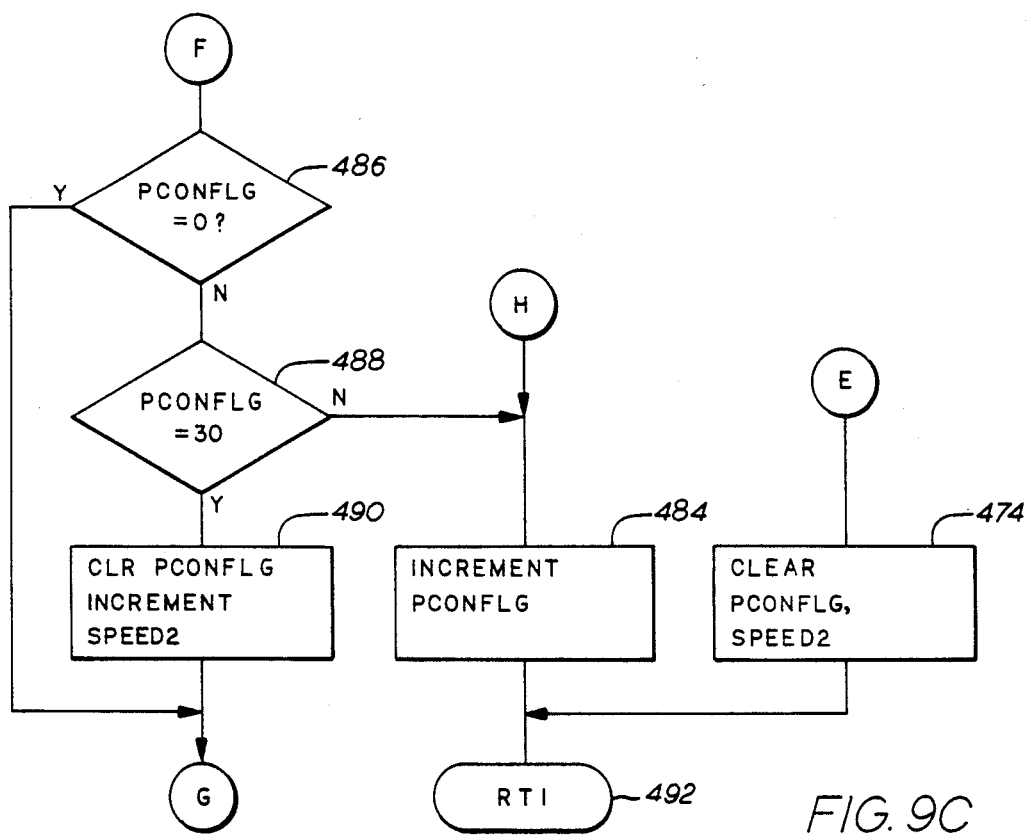
Figure 17:
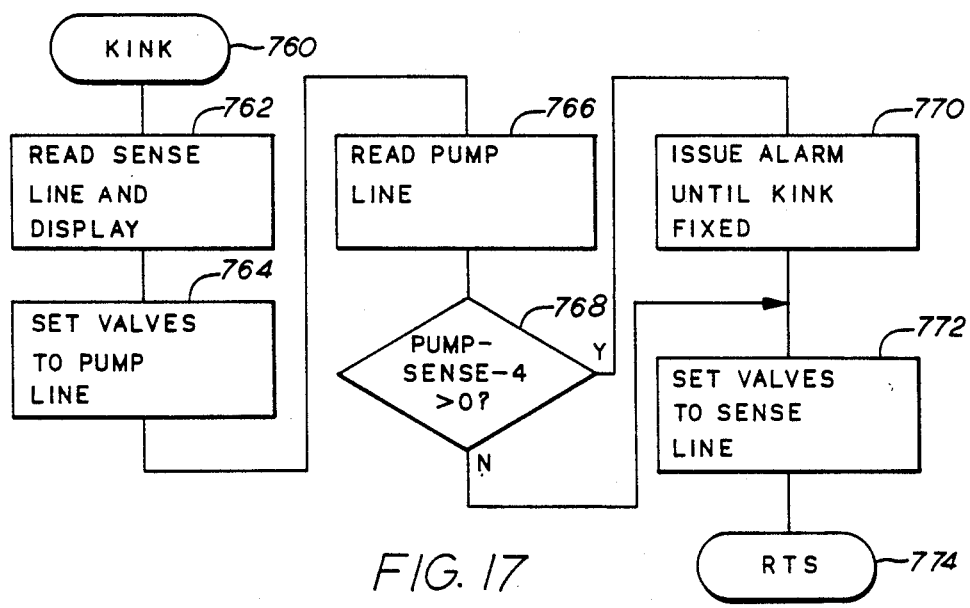
Figures 10, 22:
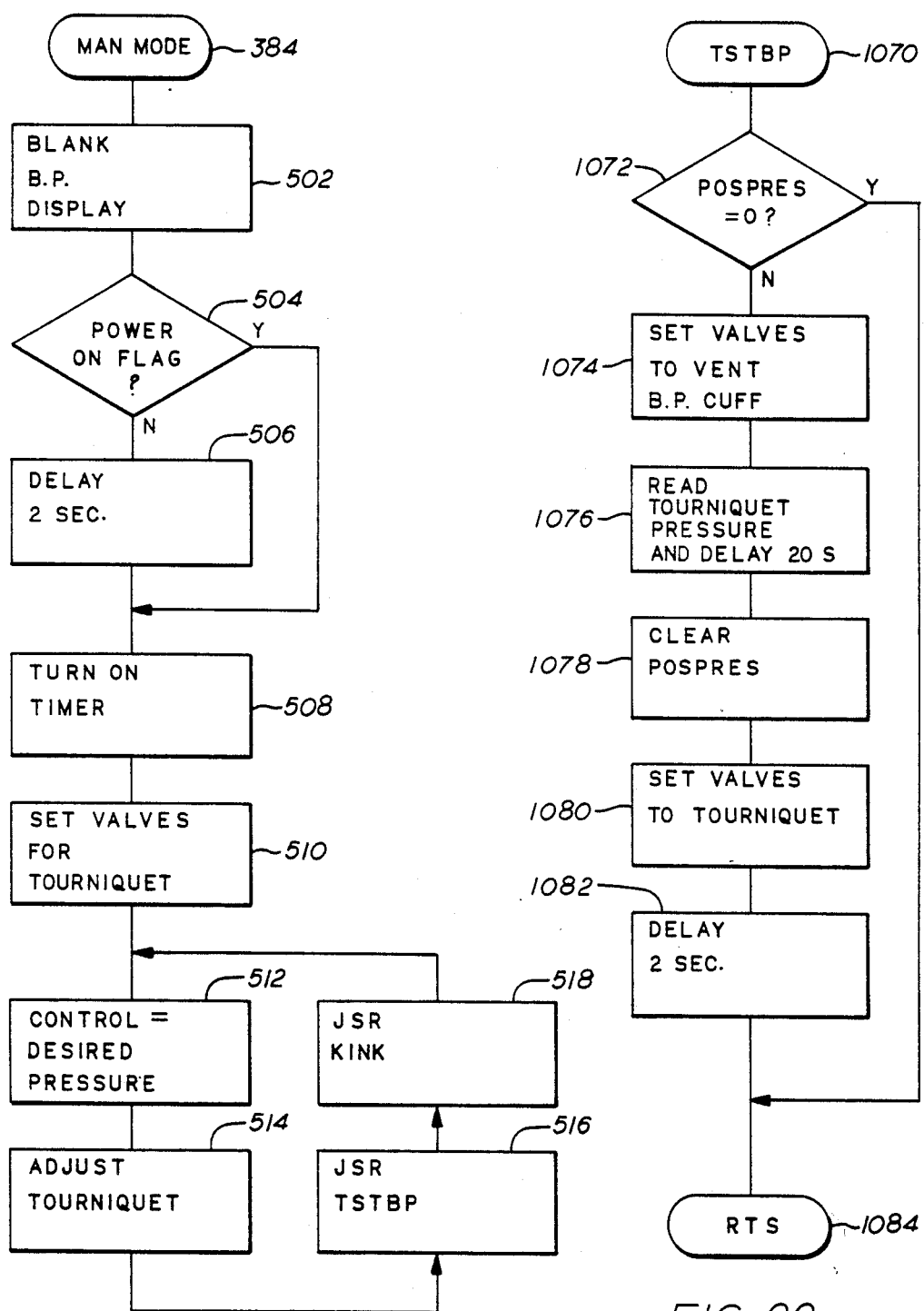
Figure 11:
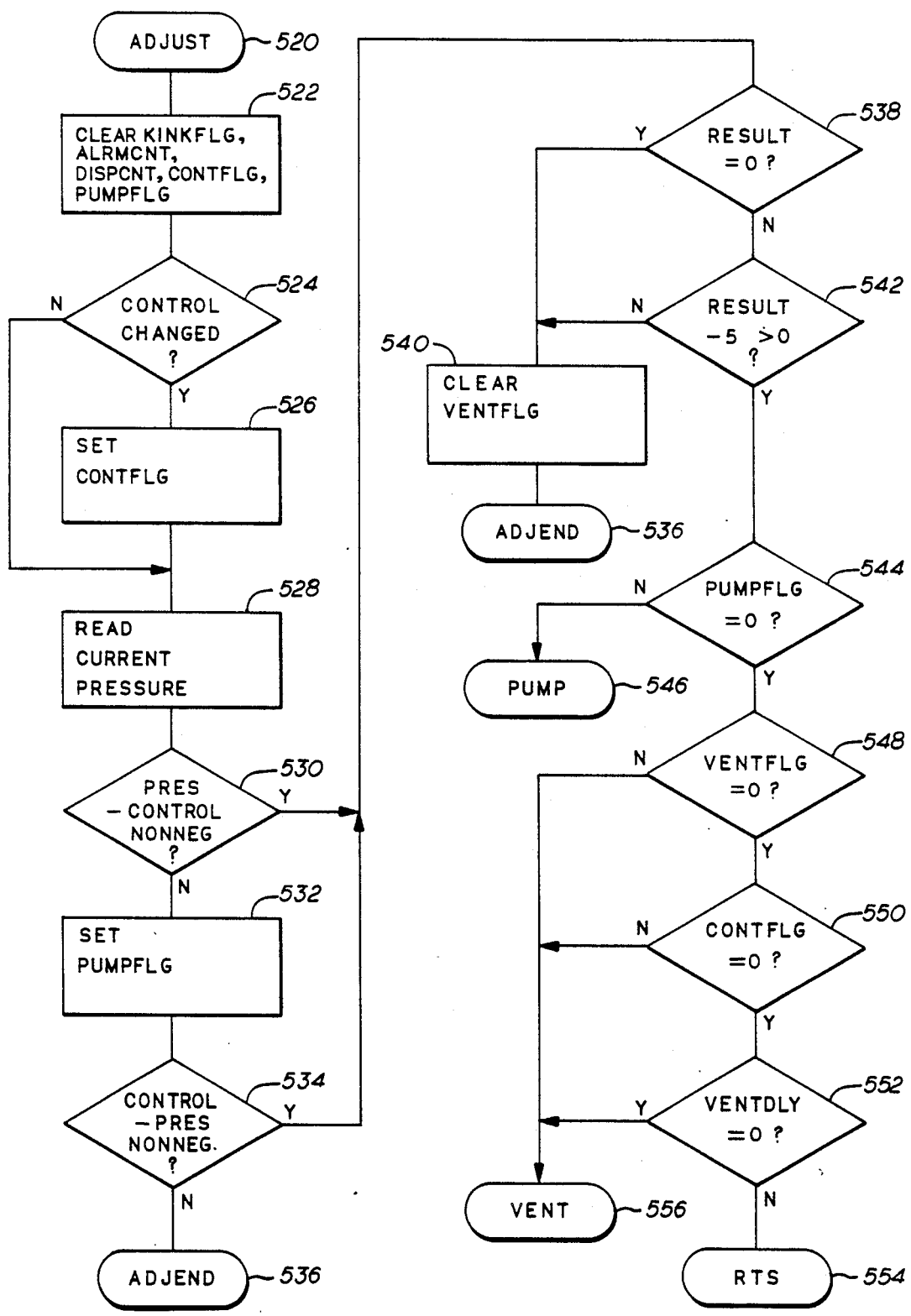

If the release switch 72 has been depressed by the operator in the off mode, tourniquet T is vented and the elapsed time is stopped. This is done via RELEASE sequence 388 (FIG. 23). The first step is step 1090 which sets the pneumatic valves 52–60 to vent the tourniquet T. Step 1092 then turns off the elapsed timer and passes control to step 1094. Step 1094 causes microprocessor 26 to determine if the reset switch 74 has been depressed. If it has been depressed, control proceeds to step 1096 which clears the elapsed time display 44 and passes control to step 1098 which is where control would have gone if the reset switch 74 had not been depressed. Step 1098 is a 100 millisecond delay followed by step 1100 which displays the tourniquet pressure using the DISPRES sequence 700. Control then proceeds to step 1098 forming a continuous loop that displays the tourniquet pressure.

F Alarms

1. ALARM Sequence

Figure 12A:
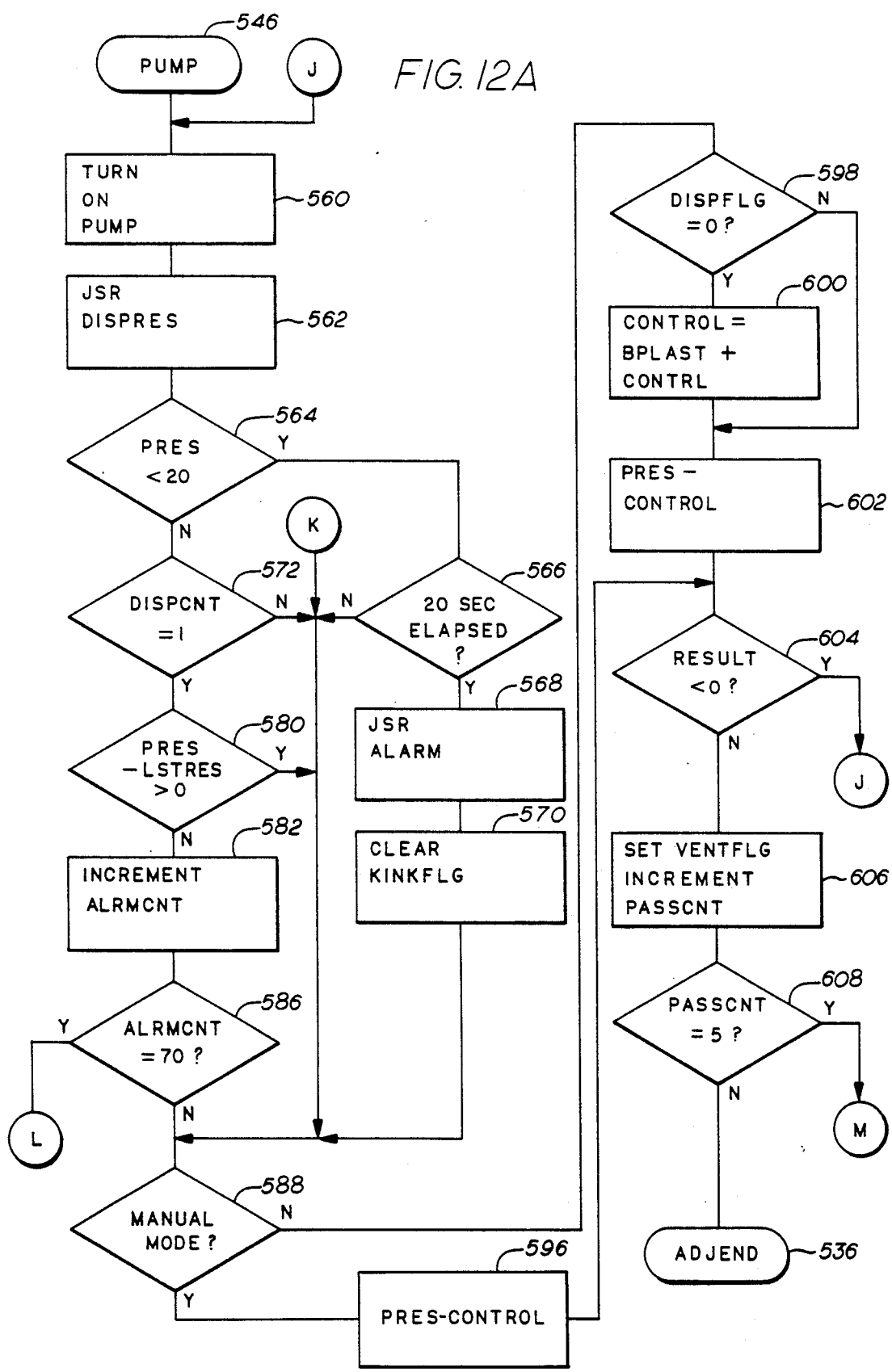
Figures 12B, 25:
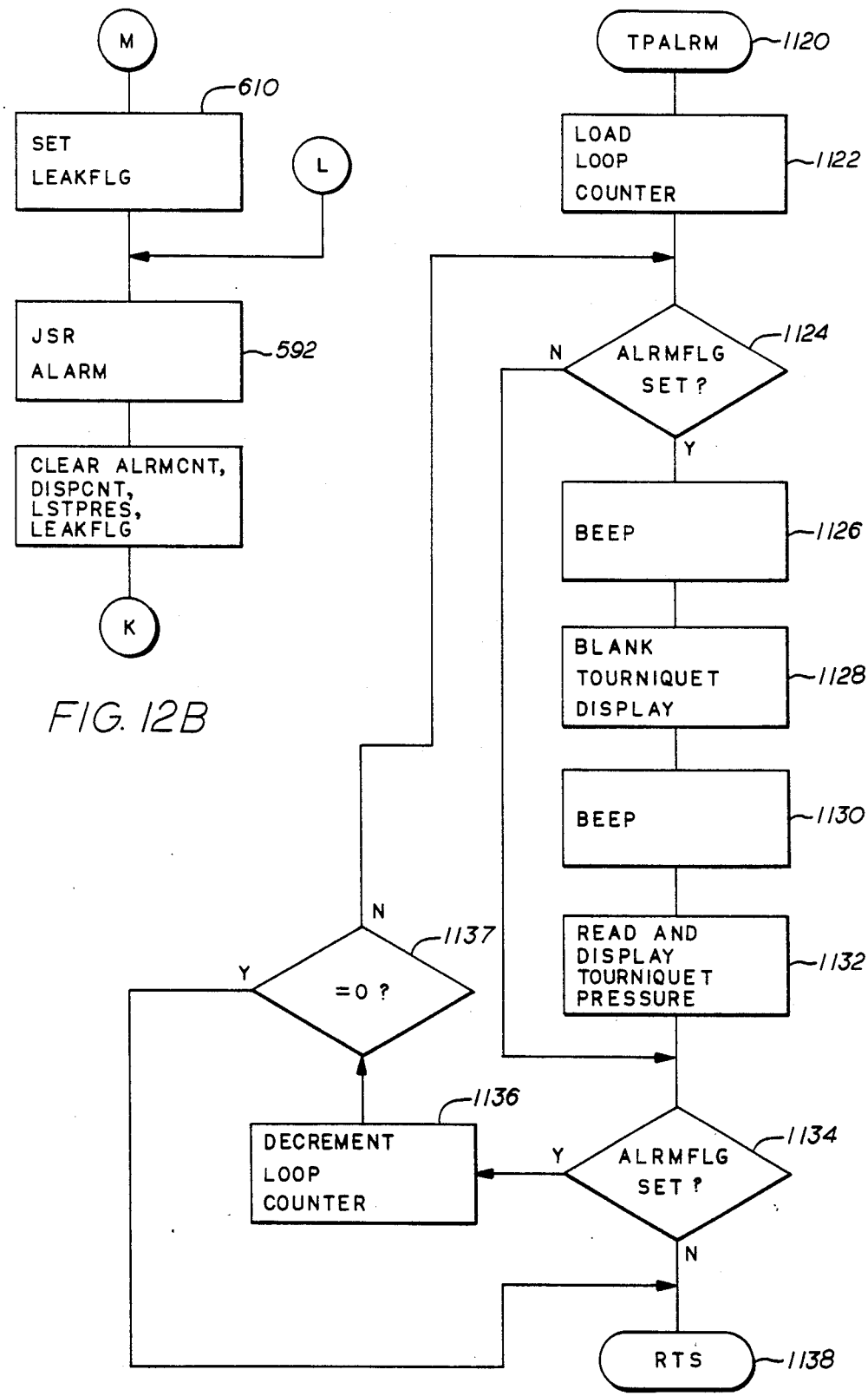
Figure 13A:
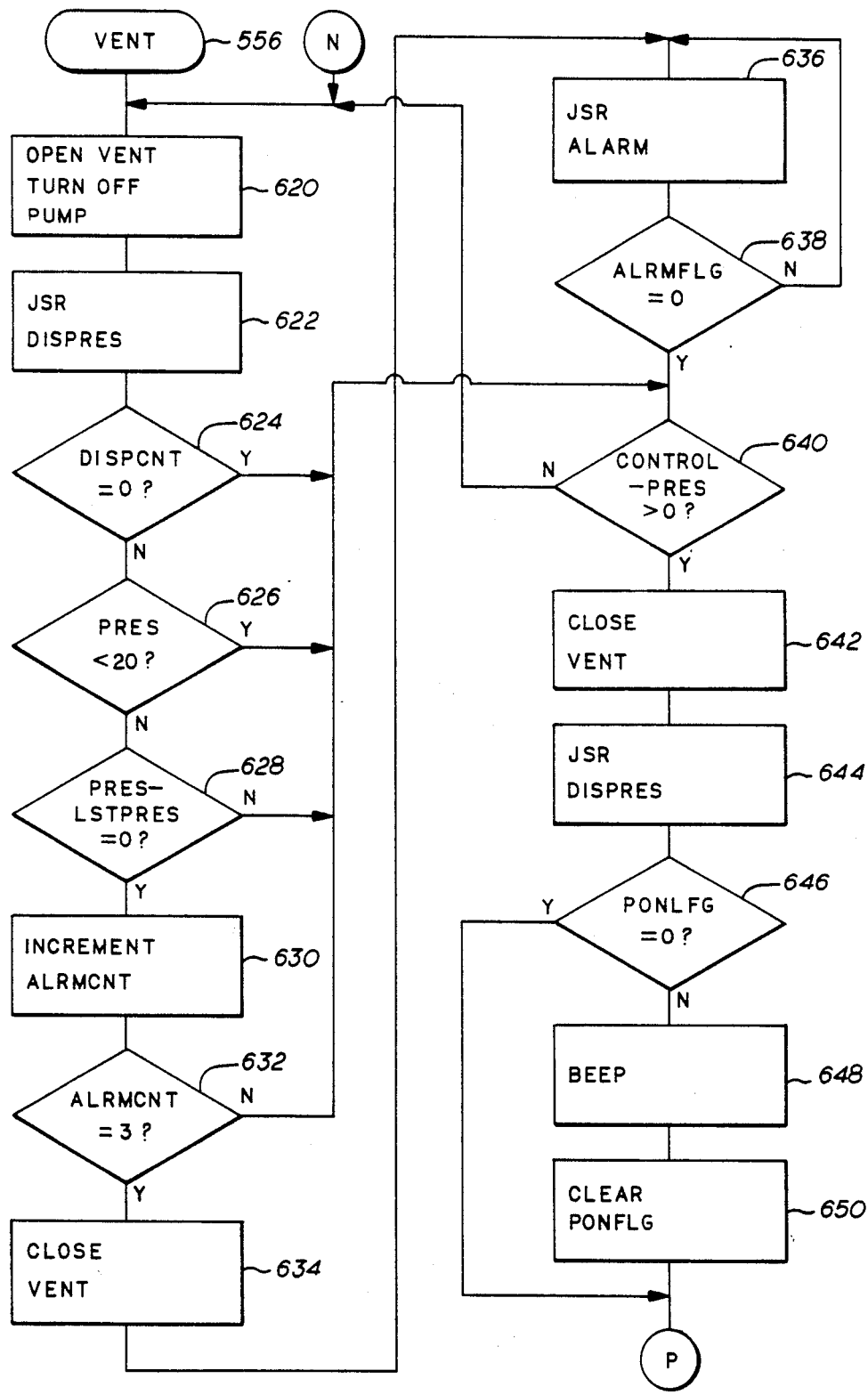
Figures 13B, 14:
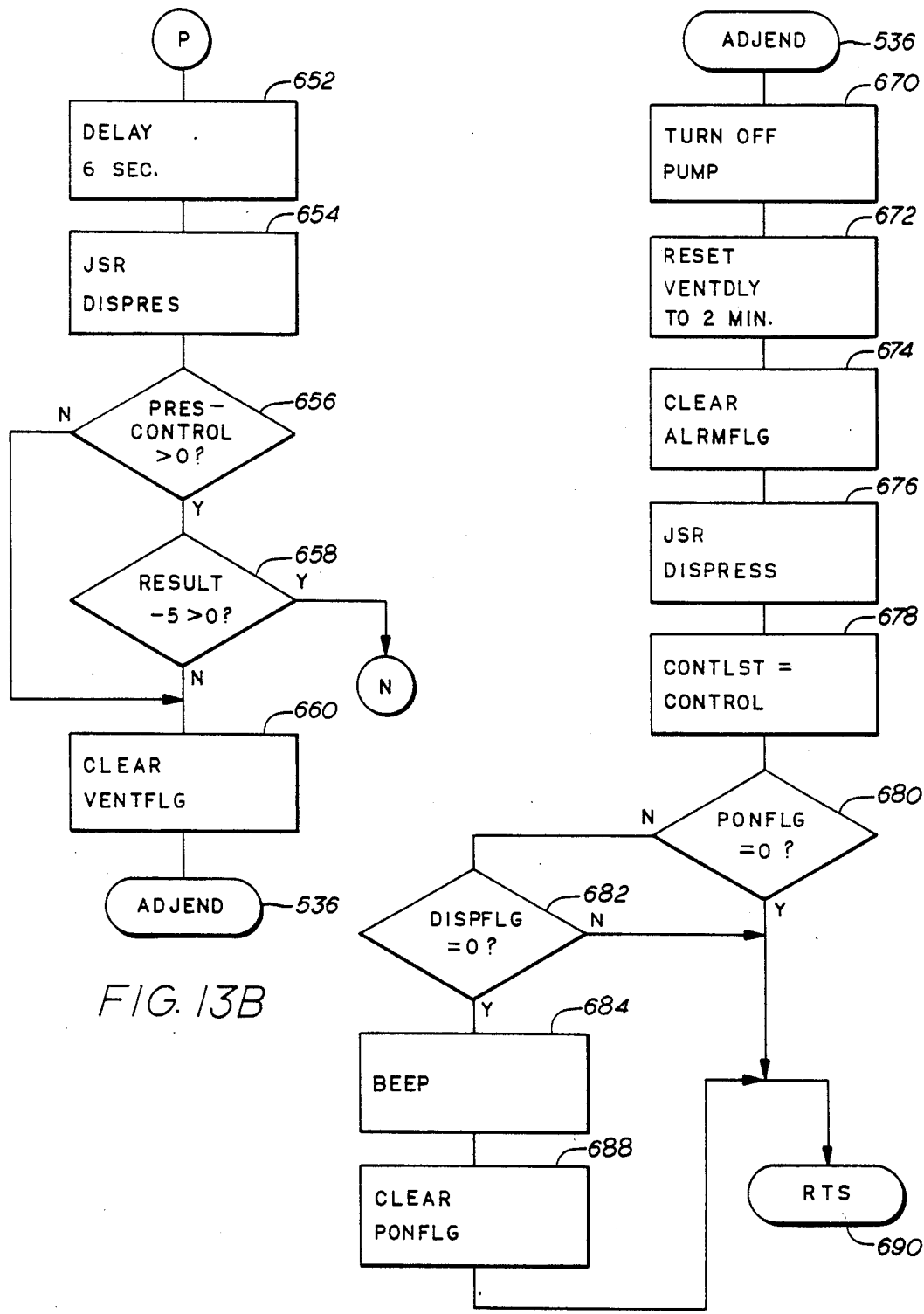
Figure 15:
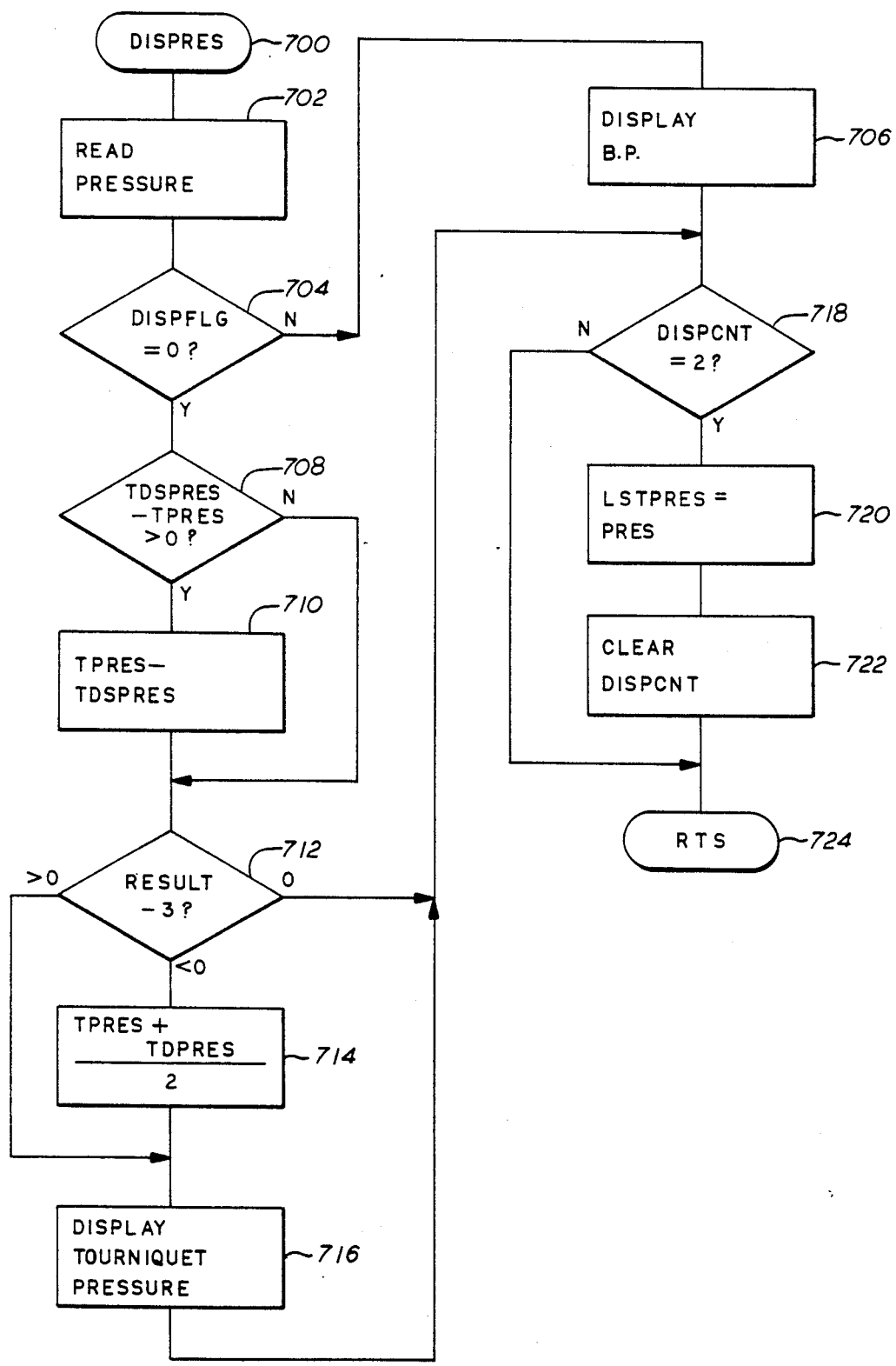
Figure 16:
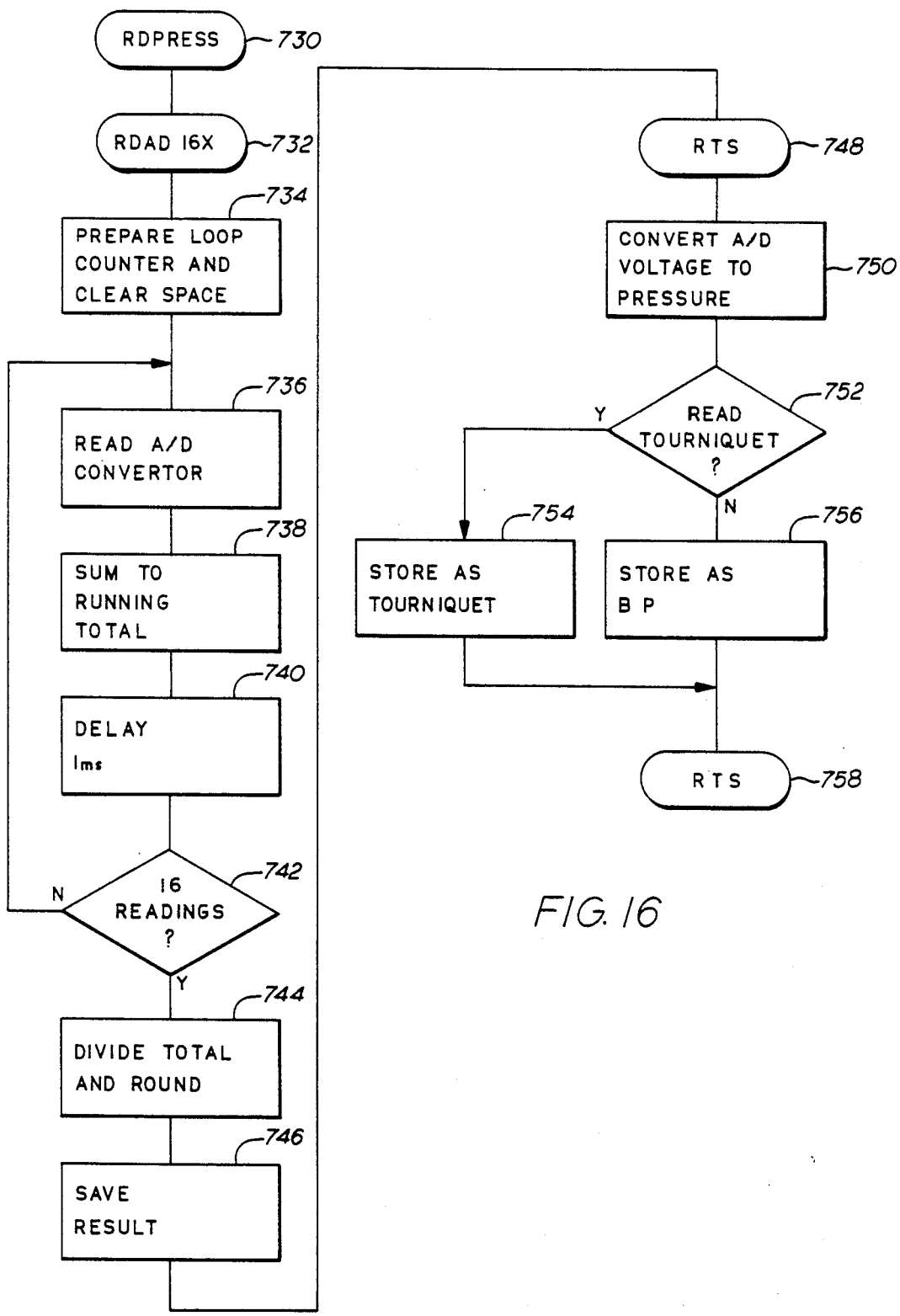
Figure 24:
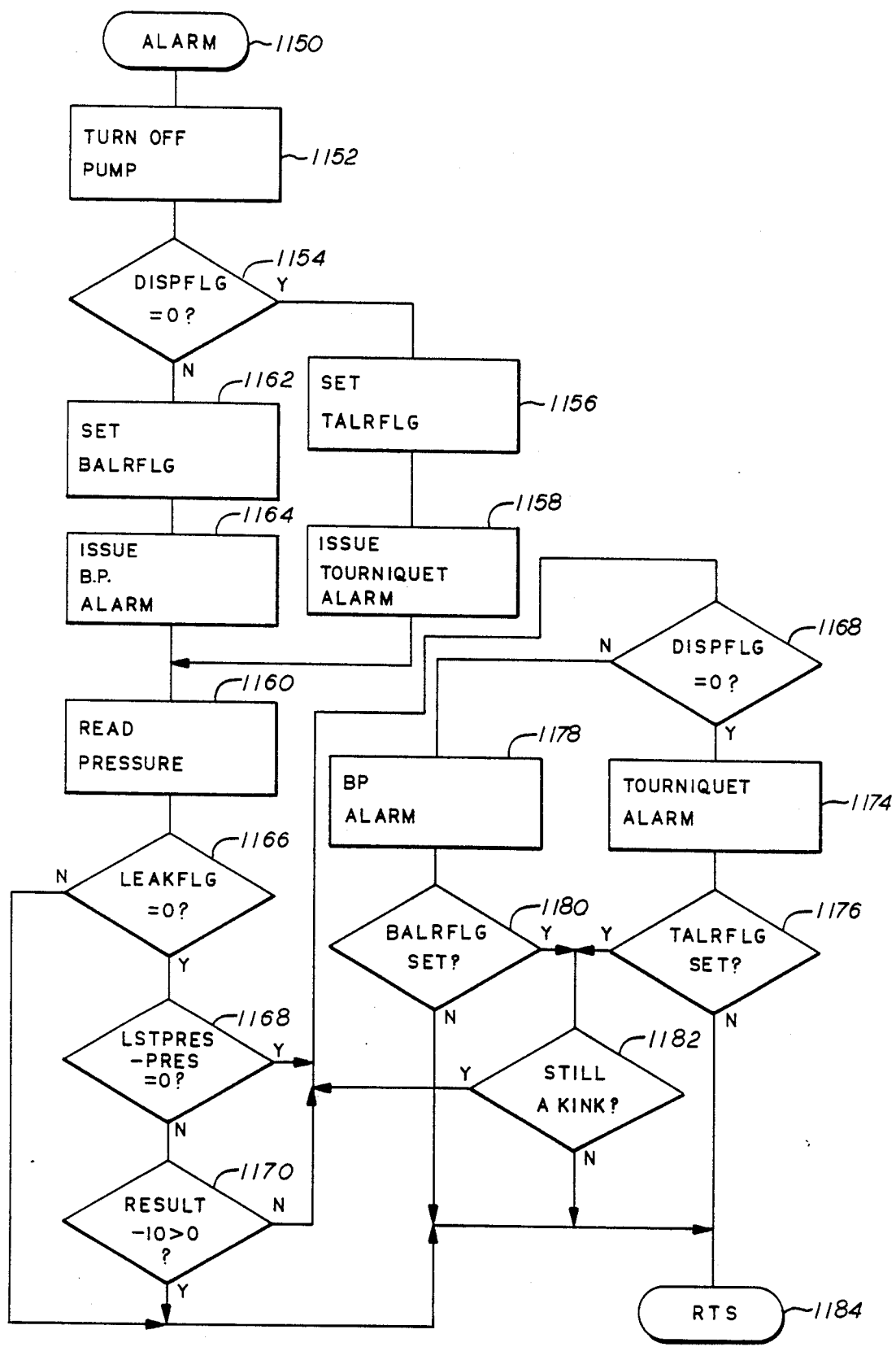
Figure 26:
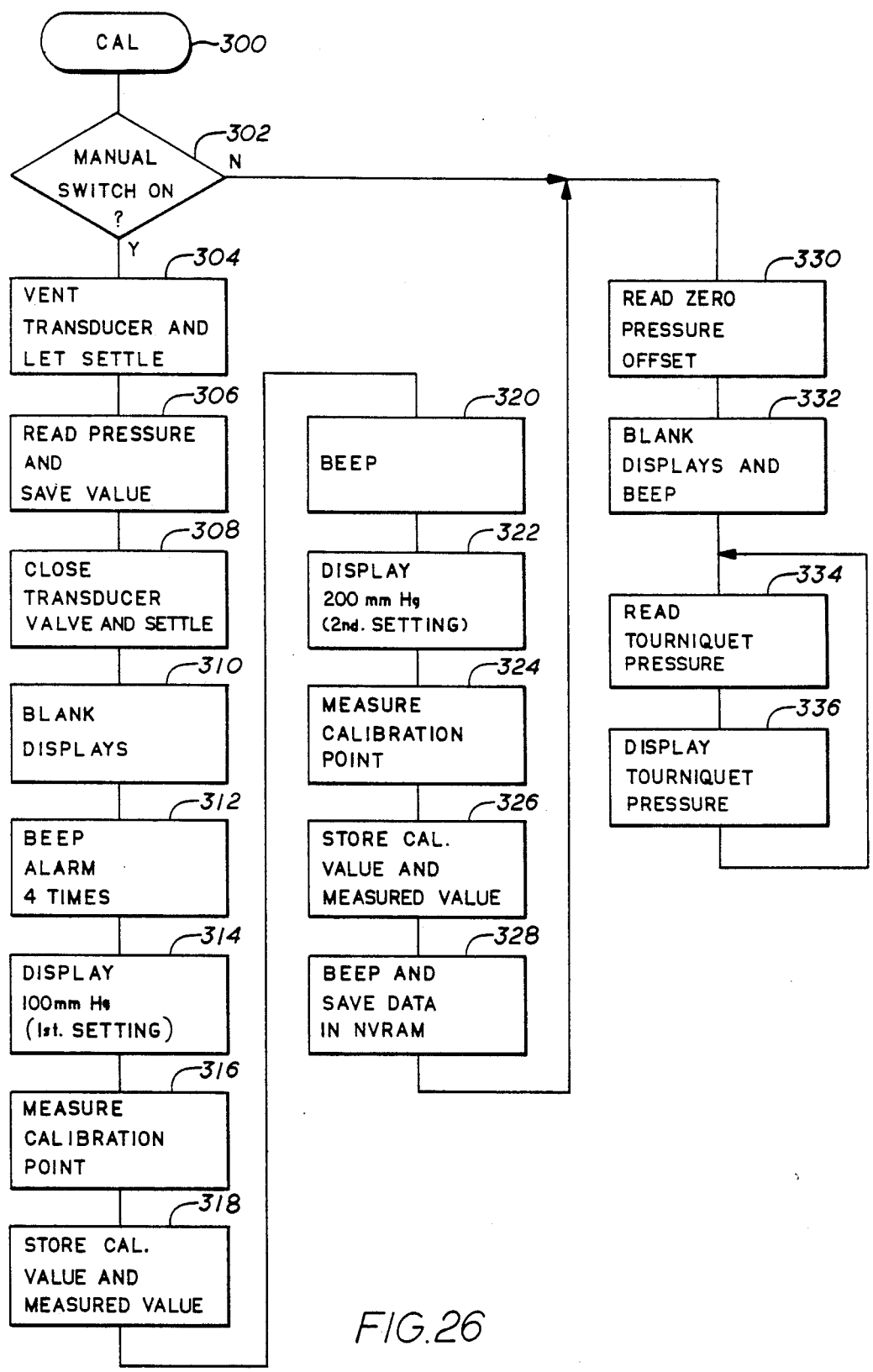
Figure 27:
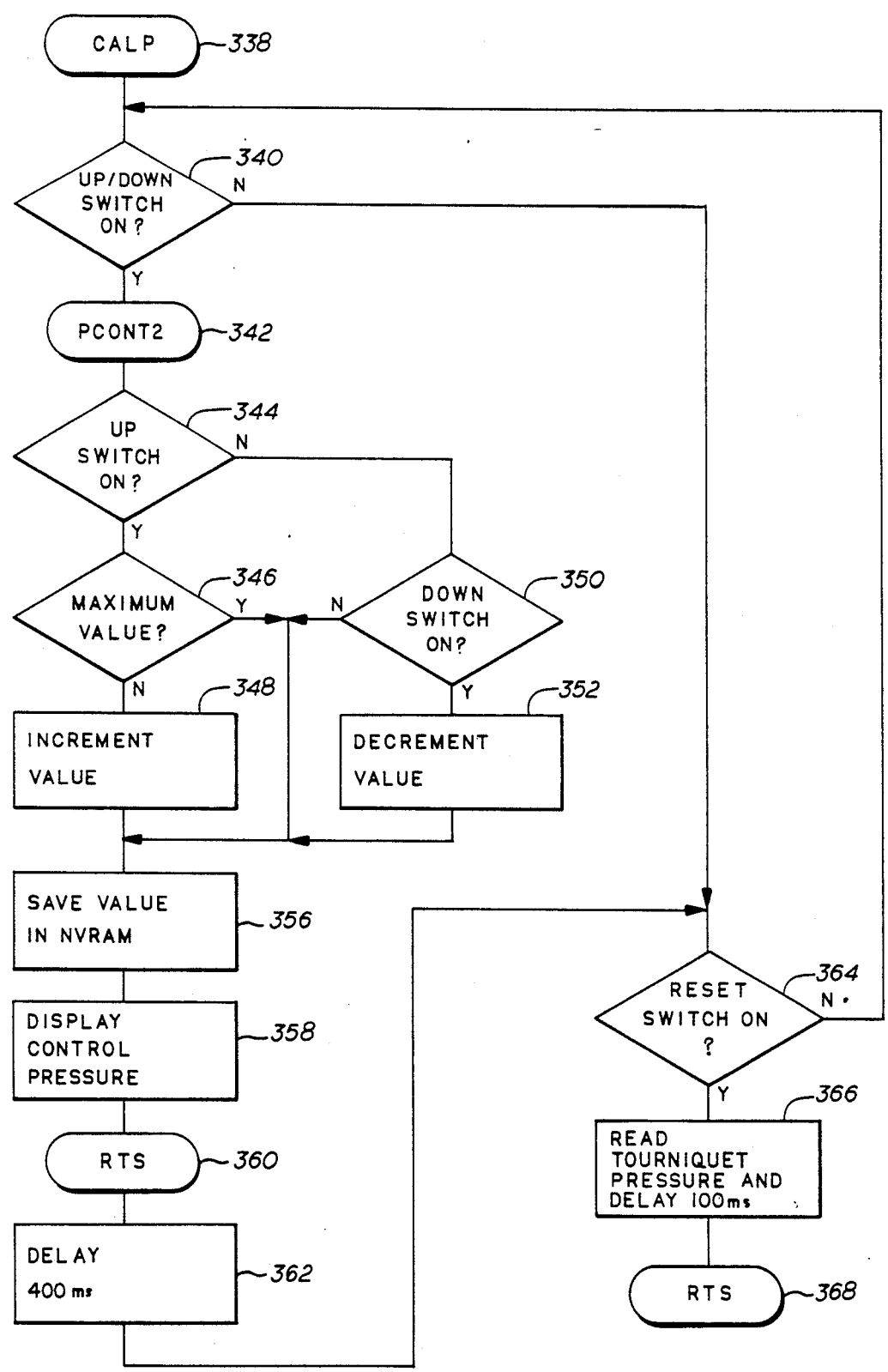

Alarms are issued using ALARM sequence 1150 (FIG. 24). The first step of the sequence is step 1152 which causes microprocessor 26 to turn off air pump 64. Step 1154 then causes microprocessor 26 to read DISPFLG to see if blood pressure or tourniquet pressure is being controlled. If blood pressure is active, step 1162 sets the blood pressure alarm flag and step 1164 issues a blood pressure alarm by causing microprocessor 26 to execute the BPALRM sequence. Control is then passed to step 1160. If tourniquet pressure is indicated by the display flag state, step 1156 sets the tourniquet alarm flag and step 1158 issues a tourniquet pressure alarm by causing microprocessor 26 to execute TPALRM sequence 1120 (FIG. 25).

Step 1160 causes microprocessor 26 to read the pressure currently available at transducer 20 as set by values 52–60 using the RDPRESS sequence 730. Step 1166 tests LEAKFLG. If LEAKFLG is set, control is transferred to step 1184. If LEAKFLG is not set, step 1168 subtracts the current pressure reading from the last pressure reading. If the result is non-zero, control passes to step 1170. Step 1170 subtracts ten from the previous result. If this result is positive, control passes to step 1184. If the result of step 1170 is zero or negative, control is passed to step 1172, which is also where control goes if the result of step 1168 is zero.

Step 1172 tests the display flag. If it is not set, step 1174 causes microprocessor 26 to issue a tourniquet pressure alarm by executing TPALRM sequence 1120. Next, step 1176 tests the tourniquet alarm flag. If the flag is set, control passes to step 1182 and if it is not set, step 1184 is the next step executed.

If the display flag was set in step 1172, step 1178 causes microprocessor 26 to issue a blood pressure alarm by executing the BPALRM sequence which will be explained later. Step 1180 then tests the blood pressure alarm flag. If the flag is set, control passes to step 1182, otherwise to step 1184.

Step 1182 causes microprocessor 26 to determine if there is a kink in the pressure lines. If so, control passes to step 1172, forming a loop. Microprocessor 26 will cause the appropriate alarm to sound and flash until the kink is cleared. If a kink is not present, control is returned to the calling sequence via step 1184.

2. TPALRM and BPALRM Sequences

There are two alarm issuance sequences, one ror tourniquet pressure and one for blood pressure. The alarm is indicated by creating beeps, flashing the appropriate display and illuminating the decimal points in the appropriate display. The tourniquet pressure alarm sequence will be explained with the differences in the blood pressure alarm sequence noted.

TPALRM sequence 1120 (FIG. 25) begins by loading a loop counter of four in step 1122. Step 1124 then causes microprocessor 26 to determine whether the tourniquet alarm flag is set or the blood pressure alarm flag if this is the blood pressure alarm sequence. If it is not set, control proceeds to step 1134, otherwise control proceeds to step 1126 which causs microprocessor 26 to provide a beep alarm signal via speaker 62. Next, step 1128 causes tourniquet display 46 or the blood pressure display 42 to be blanked as appropriate. Thereafter, another beep is provided via speaker 62 in response to step 1130. Control is then passed to step 1132 where the tourniquet pressure is read and displayed. If this is the blood pressure alarm sequence, at this time the previously determined limb pressure would be displayed. Control then proceeds to step 1134 which again causes microprocessor 26 to determine if the appropriate alarm flag is set. If the alarm flag is set, the loop counter is decremented in step 1136 and step 1137 determines if the loop counter is zero. If it is zero, control proceeds to step 1138. If it is not zero, control returns to step 1124 to form a loop. If the alarm flag was not set, control would have proceeded to step 1138 which is a return from the sequence to the appropriate calling sequence.

G. Calibration of Controller C

Control sequence 300 (FIG. 26) is the calibration sequence. Step 302 causes microprocessor 26 to determine whether the mode switch is in the manual position. If it is not in the manual position, control is transferred to step 330 which is the beginning of the calibration check section. If the switch is in the manual mode, step 304 sets the pressure transducer valve 60 to the vent position and waits for the valve to settle. The atmospheric pressure is then read by step 306 and this value is saved as the zero pressure calibration value. Step 308 closes the pressure transducer valve 60 and waits for the valve to settle. All displays are blanked in step 310 and the alarm is beeped four times in step 312. The first calibration setting of tourniquet T of 100 mmHg is displayed in control display 48 in step 314. In step 316 the exact calibration point is actually measured using the CALP sequence 338. Step 318 stores the first calibration value and the measured voltage from the pressure transducer 20 at that value. After a single beep by step 320, the second calibration setting of 200 mmHg is displayed in the control display 48 in step 322. This calibration point is measured by CALP sequence 338 in step 324. Step 326 stores the second calibration value and corresponding measured pressure transducer voltage. Controller C beeps once in step 328 and saves the obtained values in NVRAM 36.

The control sequence then proceeds to step 330 which uses the RDEERO sequence 270 to determine the zero pressure offset. All displays are blanked and a single beep is issued by step 332. The tourniquet pressure is then read using RDPRESS sequence 730. This tourniquet pressure is displayed in tourniquet pressure display 46 by step 336 and control is then passed to step 334 to initiate a closed loop which allows any given external pressure applied to tourniquet T to be read from tourniquet pressure display 46. This allows a linearity check of the unit as compared to an external reference standard.

CALP sequence 338 (FIG. 27) is used to read the external air pressure applied to tourniquet T as needed by the calibration routine. Step 340 causes microprocessor 26 to determine the status of switch 70. If switch 70 is off, control is passed to step 364. Step 364 causes microprocessor 26 to read the status of reset switch 74. If reset switch 74 is set, this indicates that the value of air applied by the external source is the same as that indicated in control pressure display 48. If switch 70 is activated, PCONT2 sequence 342 is called. In the PCONT2 sequence 342 control proceeds with step 344 which causes microprocessor 26 to read the status of switch 70. If switch 70 is in the up position, step 346 causes microprocessor 26 to determine if the calibration value has been incremented to the maximum level allowed. If it has not been incremented to the maximum, the calibration value is incremented by step 348. Step 348 then passes control to step 354, which is where control would pass if the calibration value had reached its maximum value of 450 mmHg as determined by step 346.

If switch 70 has not been in the up position, step 350 checks to see if switch 70 is in the down position. If switch 70 is in the down position, step 352 would decrement the control value and pass control to step 356 which is also where control would be passed if switch 70 is not activated. Step 356 saves the new value in NVRAM 36. The control pressure is displayed in step 358 and control is returned to the calling sequence in step 360. After a 200 millisecond delay in step 362, step 364 checks the position of reset switch 74. If reset switch is not activated, control returns to step 340 to check the position of switch 70 and thereby form a loop. If reset switch 74 is activated, control passes to step 366 which delays two seconds and reads the tourniquet pressure. Control is then passed to step 368 which returns control to the calling sequence.

In overview, to calibrate the controller C, the mode switch 68 should be in the manual position at power on or after the power on control value change. The unit will automatically read a new zero pressure value and beep the alarm four times to alert the operator to connect an external source of pressure at the setting shown in the control display 48. This setting can then be changed by using the up/down switch 70 as necessary. Hitting the reset switch 74 initiates a reading by the controller C to use this point as the first calibration point. The second calibration point is then shown in the control display 48 and can be changed using the up/down switch 70 to the value being delivered by the external supply. Activating the reset switch 70 initiates the reading of the second calibration point after which time the values are stored in the NVRAM 36 for later use. The unit then proceeds to go into a linearity check mode where the pressure applied to the tourniquet sense line 142 is displayed on the tourniquet pressure display 46 to allow the unit to be checked at alternate pressures.

IV.

Conclusion

The system of the present invention thus provides an automatic tourniquet that uses a systolic blood pressure measuring method that is sufficiently error-free to allow unattended operation with a greatly reduced danger of possible patient complications. There are three modes of operation, off, manual and automatic.

In automatic mode the controller C uses the systolic blood pressure measuring method to accurately determine the patient's pressure. A desired, settable pressure increment is added to this determined systolic pressure value to determine the desired pressure of the tourniquet T. The trourniquet pressure is then maintained at this pressure. The controller C automatically rechecks the blood pressure at given intervals or the blood pressure can be rechecked on command.

The off mode of operation keeps the volume of air in the tourniquet T constant and does not actively maintain the tourniquet pressure. If desired, the apparatus A will recheck the patient's blood pressure at given intervals, using the systolic blood pressure measuring methods as described in detail previously.

The manual mode of operation allows the tourniquet pressure to be set as desired and then the tourniquet pressure is maintained at this level.

Alarms are enabled when certain malfunction conditions or warning states exist so that the operator can correct the situation.

The foregoing disclosure and description of the invention are illustrative and explanatory thereof, and various changes in the size, shape and materials as well as in the details of the illustrated construction may be made without departing from the spirit of the invention, all such changes being contemplated to fall within the scope of the appended claims.

We claim:

1. An apparatus for automatically controlling the pressure in a pneumatic tourniquet applied to a patient in response to the systolic blood pressure of the patient, comprising:

blood pressure cuff means for applying a variable pressure to a portion of the patient;

means for varying the pressure applied by said blood pressure cuff means;

means for periodically sensing the instantaneous pressure of said cuff means and providing a signal indicative thereof;

means responsive to said instantaneous pressure signal for determining the pressure applied by said cuff means at a plurality of different values and producing a signal indicative thereof;

means responsive to said instantaneous pressure signal determining the pulsatile amplitude of the blood pressure pulses corresponding to each of the plurality of applied pressure values and producing a signal indicative thereof;

means response to said applied pressure signal and said pulsatile amplitude signal for determining the systolic blood pressure of the patient including developing an approximation of the applied pressure and pulsatile amplitude curve for the region between systolic and mean arterial pressure, determining an applied pressure where the pulsatile amplitude approximates a zero amplitude, and setting the determined zero amplitude applied pressure to be the systolic blood pressure; and tourniquet control means responsive to said set systolic blood pressure for determining desired tourniquet pressure and for maintaining said tourniquet pressure at a desired level above said set systolic blood pressure.

2. The tourniquet of claim 1, wherein said systolic blood pressure determination means further includes a means for verifying that the determined systolic blood pressure is an expected physiological condition.

3. The tourniquet of claim 2, wherein the verification means includes determining that the parameters of the developed approximation are within expected limits.

4. The tourniquet of claim 1, wherein the approximation is a linear approximation.

5. The tourniquet of claim 4, wherein the linear approximation is performed by a least squares solution.

6. The tourniquet of claim 4, wherein the linear approximation with the steepest slope within expected limits is used to determine the zero amplitude applied pressure.

7. A method for automatically controlling the pressure in a pneumatic tourniquet applied to a patient in response to the systolic blood pressure of the patient, the tourniquet including a blood pressure cuff, comprising:

applying a variable pressure to a portion of the patient using the blood pressure cuff;

varying the pressure applied by the blood pressure cuff;

periodioally sensing the instantaneous pressure of the cuff means and providing a signal indicative thereof;

determining the pressure applied by the cuff means at a plurality of different values by analyzing said instantaneous pressure signal and producing a signal indicative of the applied pressure;

the pulsatile amplitude of the blood pressure pulses corresponding to each of the plurality of applied pressure values by analyzing said instantaneous pressure signal and producing a signal indicative of the pulsatile amplitude;

determining the systolic blood pressure of the patient, by analyzing the applied pressure signal and the pulsatile amplitude signal, including developing an approximation of the applied pressure and pulsatile amplitude curve for the region between systolic and mean arterial pressure, determining an applied pressure where the pulsatile amplitude approximates a zero amplitude, and setting the determined zero amplitude applied pressure to be the systolic blood pressure; and determining the desired tourniquet pressure based the set systolic blood pressure and maintaining the tourniquet pressure at a desired level above the set systolic blood pressure.

8. The method of claim 7, wherein said systolic blood pressure determining step further includes verifying that the determined systolic blood pressure is an expected physiological condition.

9. The method of claim 8, wherein the verifying step includes determining that the parameters of the developed approximation are within expected limits.

10. The method of claim 7, wherein the approximation developed is a linear approximation.

11. The method of claim 10, wherein the linear approximation is performed by a least squares solution.

12. The method of claim 10, wherein the linear approximation with the steepest slope within expected limits is used to determine the zero amplitude applied pressure.

* * * * *